United States Patent
Branch et al.

(10) Patent No.: US 9,512,421 B1
(45) Date of Patent: Dec. 6, 2016

(54) MINIATURE ACOUSTIC WAVE LYSIS SYSTEM AND USES THEREOF

(71) Applicant: Sandia Corporation, Albuquerque, NM (US)

(72) Inventors: Darren W. Branch, Albuquerque, NM (US); Erika Cooley Vreeland, Albuquerque, NM (US); Gennifer Tanabe Smith, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 149 days.

(21) Appl. No.: 14/318,364

(22) Filed: Jun. 27, 2014

(51) Int. Cl.
| | |
|---|---|
| *C12N 13/00* | (2006.01) |
| *C12M 1/33* | (2006.01) |
| *G01N 29/036* | (2006.01) |
| *G01N 29/02* | (2006.01) |
| *H03H 9/145* | (2006.01) |
| *H03H 9/02* | (2006.01) |

(52) U.S. Cl.
CPC .............. *C12N 13/00* (2013.01); *G01N 29/02* (2013.01); *G01N 29/036* (2013.01); *H03H 9/02866* (2013.01); *H03H 9/14505* (2013.01); *G01N 2291/0255* (2013.01); *G01N 2291/0256* (2013.01); *G01N 2291/0423* (2013.01)

(58) Field of Classification Search
CPC .... C12N 13/00; G01N 29/02; G01N 29/036; G01N 2291/0255; G01N 2291/0256; G01N 2291/0423; H30H 9/14505; H30H 9/02866
USPC ...................................................... 435/306.1
See application file for complete search history.

(56) References Cited

U.S. PATENT DOCUMENTS

| | | | |
|---|---|---|---|
| 6,168,948 B1 | 1/2001 | Anderson et al. | |
| 6,887,693 B2 | 5/2005 | McMillan et al. | |
| 7,785,868 B2 | 8/2010 | Yuan et al. | |
| 7,878,063 B1 | 2/2011 | Cular et al. | |
| 7,942,568 B1 | 5/2011 | Branch et al. | |
| 8,425,749 B1 | 4/2013 | Ravula et al. | |
| 8,436,509 B1 | 5/2013 | Branch | |
| 8,525,619 B1 | 9/2013 | Olsson et al. | |
| 8,669,688 B1 | 3/2014 | Branch | |
| 8,709,791 B2 | 4/2014 | Larson et al. | |
| 9,096,823 B1 * | 8/2015 | Branch | C12M 47/06 |
| 2010/0260984 A1 * | 10/2010 | Wu | B01J 19/0046 428/209 |
| 2011/0053139 A1 | 3/2011 | Larson et al. | |

OTHER PUBLICATIONS

U.S. Appl. No. 12/872,919, filed Aug. 31, 2010, Vreeland et al.
Adams JD et al., "Integrated acoustic and magnetic separation in microfluidic channels," *Appl. Phys. Lett.* Dec. 21, 2009;95(25):254103 (3 pages.).
Adams JD et al., "Tunable acoustophoretic band-pass particle sorter," *Appl. Phys. Lett.* Aug. 9, 2010;97(6):064103 (3 pages).

(Continued)

*Primary Examiner* — Michael Hobbs
(74) *Attorney, Agent, or Firm* — Aman Talwar

(57) ABSTRACT

The present invention relates to an acoustic lysis system including a disposable cartridge that can be reversibly coupled to a platform having a small, high-frequency piezoelectric transducer array. In particular, the system releases viable DNA, RNA, and proteins from human or bacterial cells, without chemicals or additional processing, to enable high-speed sample preparation for clinical point-of-care medical diagnostics and use with nano/microfluidic cartridges. Also described herein are methods of making and using the system of the invention.

25 Claims, 9 Drawing Sheets

(56) References Cited

OTHER PUBLICATIONS

Ai Y et al., "Separation of *Escherichia coli* bacteria from peripheral blood mononuclear cells using standing surface acoustic waves," *Anal. Chem.* Oct. 1, 2013;85(19):9126-34.
Arora A et al., "Latest developments in micro total analysis systems," *Anal. Chem.* Jun. 15, 2010;82(12):4830-47.
Auroux PA et al., "Micro total analysis systems. 2. Analytical standard operations and applications," *Anal. Chem.* Jun. 15, 2002;74(12):2637-52.
Belgrader P. et al., "A minisonicator to rapidly disrupt bacterial spores for DNA analysis," *Anal. Chem.* Oct. 1, 1999;71(19):4232-6.
Bloomfield PE et al., "Experimental study of the acoustical properties of polymers utilized to construct PVDF ultrasonic transducers and the acousto-electric properties of PVDF and P(VDF/TrFE) films," *IEEE Trans. Ultrason. Ferroelectr. Freq. Control* 2000;47(6):1397-405.
Boom R et al., "Rapid and simple method for purification of nucleic acids," *J. Clin. Microbiol.* Mar. 1990;28(3):495-503.
Branch DW et al., "Intelligent front-end sample preparation tool using acoustic streaming," Sandia Report No. SAND2009-6193, Sep. 2009 (70 pages).
Cady NC et al., "Nucleic acid purification using microfabricated silicon structures," *Biosens. Bioelectron.* Oct. 30, 2003;19(1):59-66.
Chandler DP et al., "Continuous spore disruption using radially focused, high-frequency ultrasound," *Anal. Chem.* Aug. 1, 2001;73(15):3784-9.
Cheng J et al., "Preparation and hybridization analysis of DNA/RNA from *E. coli* on microfabricated bioelectronics chips," *Nat. Biotechnol.* Jun. 1998;16:541-6.
Cooley EJ et al., "A versatile DNA extraction system for rapid sample preparation using acoustic lysis," Biomed. Eng. Soc. (BMES) held on Oct. 4, 2008 in St. Louis, MO (1 page).
Culbertson CT et al., "Micro total analysis systems: Fundamental advances and biological applications," *Anal. Chem.* 2014;86:95-118.
De Cock KM et al., "Will DOTS do it? A reappraisal of tuberculosis control in countries with high rates of HIV infection," *Int. J. Tuberc. Lung Dis.* Jun. 1999.;3(6):457-65.
Dion JL et al., "Exact one-dimensional computation of ultrasonic transducers with several piezoelectric elements and passive layers using the transmission line analogy," *IEEE Trans. Ultrason. Ferroelectr. Freq. Control* 1997;44(5):1120-31.
Dittrich PS et al., "Lab-on-a-chip: Microfluidics in drug discovery," *Nat. Rev. Drug Discov.* Mar. 2006;5(3):210-8.
Gal-Mor O et al., "Pathogenicity islands: A molecular toolbox for bacterial virulence," *Cell. Microbiol.* Nov. 2006;8(11):1707-19.
Gandhi NR et al., "Extensively drug-resistant tuberculosis as a cause of death in patients co-infected with tuberculosis and HIV in a rural area of South Africa," *Lancet* Nov. 4, 2006;368(9547):1575-80.
Jagannathan H et al., "Micro-fluidic channels with integrated ultrasonic transducers," *IEEE Ultrason. Symp.* 2001;2:859-62.
Jung B et al., "Acoustic particle filter with adjustable effective pore size for automated sample preparation," *Anal. Chem.* Nov. 15, 2008;80(22):8447-52.
Kovarik ML et al., "Micro total analysis systems: Fundamental advances and applications in the laboratory, clinic, and field," *Anal. Chem.* 2013;85:451-72.
Kovarik ML et al., "Micro total analysis systems for cell biology and biochemical assays," *Anal. Chem.* 2012;84:516-40.
Lagally ET et al., "Integrated portable genetic analysis microsystem for pathogen/infectious disease detection," *Anal. Chem.* Jun. 1, 2004;76(11):3162-70.
Lee M et al., "Reversible capture of genomic DNA by a Nafion-coated electrode," *Anal. Biochem.* Sep. 15, 2008;380(2):335-7.
Lee WG et al., "Nano/Microfluidics for diagnosis of infectious diseases in developing countries," *Adv. Drug Deliv. Rev.* Mar. 18, 2010;62(4-5):449-57.
Marentis TC et al., "Microfluidic sonicator for real-time disruption of eukaryotic cells and bacterial spores for DNA analysis," *Ultrasound Med. Biol.* Sep. 2005;31(9):1265-77.
Moré MI et al., "Quantitative cell lysis of indigenous microorganisms and rapid extraction of microbial DNA from sediment," *Appl. Environ. Microbiol.* May 1994;60(5):1572-80.
Nan L et al., "Emerging microfluidic devices for cell lysis: A review," *Lab Chip* Feb. 17, 2014;14(6):1060-73.
Palomino JC et al., "Rapid culture-based methods for drug-resistance detection in *Mycobacterium tuberculosis*," *J. Microbiol. Methods* Oct. 2008;75(2):161-6.
Raviglione MC et al., "XDR tuberculosis—Implications for global public health," *N. Engl. J. Med.* Feb. 15, 2007;356(7):656-9.
Ravula SK et al., "A microfluidic system combining acoustic and dielectrophoretic particle preconcentration and focusing," *Sens. Actuat. B* 2008;130:645-52.
Reboud J et al., "Shaping acoustic fields as a toolset for microfluidic manipulations in diagnostic technologies," *Proc. Nat'l Acad. Sci. USA* Sep. 18, 2012;109(38):15162-7.
Reyes DR et al., "Micro total analysis systems. 1. Introduction, theory, and technology," *Anal. Chem.* 2002;74:2623-36.
Ríos Á et al., "Sample preparation for micro total analytical systems (μ-TASs)," *Trends Anal. Chem.* 2013;43:174-88.
Sandia National Laboratories, "CleanBurst$^{TM}$: Rapid acoustic lysis for point-of-care diagnostics," Sandia Report No. SAND2013-5819P, 2013 (2 pages).
Shi J et al., "Continuous particle separation in a microfluidic channel via standing surface acoustic waves (SSAW)," *Lab Chip* Dec. 7, 2009;9(23):3354-9.
Shung KK et al., "Piezoelectric materials for high frequency medical imaging applications: A review," *J. Electroceram.* 2007;19:139-45.
Shusteff M, "Rapid automated sample preparation for biological assays," Lawrence Livermore Report No. LLNL-TR-468393, Jan. 2011 (7 pages).
Taylor MT et al., "Lysing bacterial spores by sonication through a flexible interface in a microfluidic system," *Anal. Chem.* 2001;73:492-6.
Vilkner T et al., "Micro total analysis systems. Recent developments," *Anal. Chem.* 2004;76:3373-86.
West J et al., Micro total analysis systems: Latest achievements, *Anal. Chem.* Jun. 15, 2008;80(12):4403-19.
Whitten DG et al., "Cooperative self-assembly of cyanines on carboxymethylamylose and other anionic scaffolds as tools for fluorescence-based biochemical sensing," *Pure Appl. Chem.* 2006;78(12):2313-23.
Wolfe KA et al., "Toward a microchip-based solid-phase extraction method for isolation of nucleic acids," *Electrophoresis* Mar. 2002;23(5):727-33.
Yang AHJ et al., "Acoustophoretic sorting of viable mammalian cells in a microfluidic device," *Anal. Chem.* Dec. 18, 2012;84(24):10756-62.
Yeo Ly et al., "Surface acoustic wave microfluidics," *Annu. Rev. Fluid Mech.* 2014;46:379-406.
Yeo Ly et al., "Ultrafast microfluidics using surface acoustic wave," *Biomicrofluidics* Jan. 2, 2009;3(1):12002 (23 pages).
Zhang GQ et al., "Liquid streaming by high-frequency ultrasonic waves," *Jpn. J. Appl. Phys.* 1996;35:3248-50.

\* cited by examiner

MINIATURE ACOUSTIC WAVE LYSIS SYSTEM AND USES THEREOF

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to the lysis of biological cells and, in particular, to miniature acoustic cell lysis systems for use with point-of-care diagnostics (e.g., for the detection of infectious targets).

BACKGROUND OF THE INVENTION

Most biosensors in today's market and in research and development require a critical sample preparation procedure prior to analysis of cellular contents, such as nucleic acids and proteins. Ideally, sample preparation should minimize alterations to the sample (e.g., minimize chemical modification or mechanical damage to the sample), while also being easy to use, rapid, and cost-effective. Further, when the test sample is potentially hazardous, the biosensor should allow for containment and disposal of the sample after testing.

In particular, such sample preparation technologies should be compatible with point-of-care (POC) and nano/microfluidic devices. POC diagnostics offer great potential to detect and monitor infectious diseases at resource-limited settings because POC diagnostics can be taken to remote locations, decreasing the need for large decentralized diagnostic facilities (Lee W G et al., "Nano/microfluidics for diagnosis of infectious diseases in developing countries," *Adv. Drug Deliv. Rev.* 2010 Mar. 18; 62(4-5):449-57). In addition, such POC and miniaturized fluidic devices can provide disposability, cost effectiveness, ease of use, and portability (Huckle D, "Point-of-care diagnostics: An advancing sector with nontechnical issues," *Expert Rev. Mol. Diagn.* 2008 November; 8(6):679-88). Any proposed sample preparation technology should also be consistent with these desired POC characteristics.

One sample preparation step includes lysing of whole cell samples. Commercial acoustic lysing systems require large containers to hold fluids containing biological cells in proximity to an acoustic wave source. These containers are often tubes that only process large volumes and cannot be interfaced with nano/microfluidic POC devices, which generally process small sample volumes.

One particular challenge includes rapid and accurate detection of *Mycobacterium tuberculosis* (MTB) and drug-resistant forms thereof. MTB infects approximately one-third of the world's population. Eight million new cases of TB occur each year, accounting for approximately 7% of all deaths and 26% of all avoidable adult deaths in developing countries (De Cock K M et al., "Will DOTS do it? A reappraisal of tuberculosis control in countries with high rates of HIV infection," *Int. J. Tuberc. Lung Dis.* 1999 June; 3(6):457-65). Multi drug-resistant (MDR) and extensively drug-resistant (XDR) strains have also relentlessly developed, reaching epidemic proportions in much of the developing world (Raviglione M C et al., "XDR tuberculosis— Implications for global public health," *N. Engl. J. Med.* 2007 Feb. 15; 356(7):656-9).

A beneficial diagnostic system for MTB detection should be rapid, accurate, inexpensive, and clinically useful. Given the contagious nature of such MTB samples, POC devices and sample processing components are preferably disposable to protect the end-users from exposure to biohazardous waste. For on-site testing, the diagnostic system should have an integrated sample preparation component. The first step in sample preparation is to release MTB DNA for PCR identification, sequencing, and susceptibility profiling through mutation analysis. MTB provides several challenges as it is known to resist chemical and enzymatic lysing strategies and noted for its long-term (i.e., a few weeks) stability in a dry state, both of which challenge existing DNA extraction methods.

Therefore, a need remains for technology that releases cellular contents in a format compatible with miniaturized POC devices. In particular, there is a need for miniature acoustic lysing methods that can disrupt resilient cells (e.g., MTB) without the use of heat, chemicals, or enzymes that can interfere with PCR and DNA sequencing methods. Such systems and methods would also be beneficial if it minimized power consumption.

SUMMARY OF THE INVENTION

The present invention encompasses systems that dramatically shrink the footprint of the current cellular lysis technology while combining it with the ability to integrate various assays into a single device assay, for example, integration with devices for polymerase chain reaction (PCR) amplification with capillary electrophoretic analysis and laser-excited fluorescence detection (see, e.g., Dittrich P S et al., "Lab-on-a-chip: Microfluidics in drug discovery," *Nat. Rev. Drug Discov.* 2006 March; 5(3):210-8; West J et al., "Micro total analysis systems: Latest achievements," *Anal. Chem.* 2008 Jun. 15; 80(12):4403-19; and Lagally E T et al., "Integrated portable genetic analysis microsystem for pathogen/infectious disease detection," *Anal. Chem.* 2004 Jun. 1; 76(11):3162-70).

In particular, the system employs high-frequency acoustic waves that rapidly disrupt cellular membranes without chemical treatment, thereby releasing the intracellular material without damage or undesirable physical or chemical modification. By releasing the intracellular contents without the need for chemicals and simultaneously preserving the biological structure, the analysis does not require large laboratory equipment or time-consuming processing. The system can use a very compact multichannel format including a separate miniature acoustic transducer for each channel of a multichannel cartridge. Since the acoustic waves are applied remotely, the multichannel cartridge can be reversibly coupled to a transducer array and discarded after use. Each acoustic transducer can be controlled separately and operated over a wide range of power settings for tailored operation. The technology is easily interfaced with existing nano/microfluidic and POC diagnostic technologies for the purpose of creating disposable, inexpensive, portable, and easy-to-use devices for global health and research applications.

With the invention, raw biological samples can be better handled on-chip, reducing sample loss, while enabling small volume processing and fast analysis compared to conventional methods. The invention can disrupt (lyse) the cellular membranes of even the most difficult bacteria, such as MTB, in seconds. This technology fills a significant gap in the diagnostic toolset for infectious disease analysis by providing a way to gain rapid access to genomic material (DNA).

For genomic analysis (e.g., for example to distinguish between less pathogenic bacteria and those carrying pathogenicity islands or mutations conferring drug-resistance), the current extraction techniques require significant manual intervention and consumables. This situation leads to limitations that are especially relevant for the unattended, timely detection of biological targets without continued reliance on large laboratory equipment. By avoiding harsh chemicals or reagents that interfere with genomic analysis methods and can denature proteins, the invention enables lysed samples to be processed immediately.

Accordingly, the invention features a miniature acoustic cell lysis system including: a cartridge including a plurality of channels (e.g., where each channel is configured to receive one or more test samples); a platform including a transducer array, which includes a plurality of acoustic transducers; and a thermal exchange layer configured to be disposed between the cartridge and the transducer array. In some embodiment, the transducer array is configured to be coupled reversibly to the cartridge. In further embodiments, each acoustic transducer is configured to be disposed beneath each channel and is adapted to propagate an acoustic wave in the channel, thereby generating localized acoustic pressure to lyse a cell by acoustic pressure.

In some embodiments, the thermal exchange layer includes aluminum nitride, silicon carbide, silicon nitride, boron nitride, beryllium oxide, copper, silver, gold, graphene, diamond, thermal epoxy, stainless steel, or a composite thereof.

In other embodiments, the thermal exchange layer is affixed to the platform and is disposed above the transducer array. In yet other embodiments, the thermal exchange layer is affixed to the cartridge and is disposed beneath the plurality of channels.

In some embodiments, the cartridge is disposable and/or the platform is reversibly coupled to the cartridge.

In further embodiments, the system includes a platen configured to maintain the cartridge in a fixed relationship with the transducer array and/or to enable fluidic communication with the channel.

In some embodiments, the system further includes a heatsink disposed beneath the transducer array.

In other embodiments, the system further includes a solid support configured to be integrated within the cartridge and to be in fluidic communication with at least one of the plurality of channels. Exemplary solid supports include a filter, a bead, a membrane, or a gel exclusion media, as well as any other described herein.

In some embodiments, the system further includes a pumping system in fluidic communication with the inlet.

In some embodiments, the platform further includes a transducer substrate including a plurality of electrodes. In other embodiments, each electrode is electrically connected to each acoustic transducer, and a radiofrequency driver board including one or more contact pads is configured to be electrically connected to each of the plurality of electrodes. In yet other embodiments, the platform further includes a radiofrequency circuit configured to provide a radiofrequency signal to the driver board.

In some embodiments, the system further includes an acoustic reflector disposed on a top surface of at least one channel. In further embodiments, the acoustic reflector is adapted to create a standing wave within the channel and between the acoustic reflector and at least one acoustic transducer (e.g., disposed on the opposing side or surface of the acoustic reflector). The acoustic reflector can be formed from any useful material, e.g., glass, a metal, a mirror, etc.

The cartridge can have any useful components. In one embodiment, the cartridge includes a channel layer including the plurality of channels, where each channel includes an inlet portion and an outlet portion; a top layer disposed above the channel layer, where the top layer includes a plurality of inlet ports in fluidic communication with each inlet portion and a plurality of outlet ports in fluidic communication with each outlet portion; and/or a filter layer disposed between the channel layer and top layer. In particular embodiments, the filter layer includes a plurality of solid supports, and each solid support is configured to be in fluidic communication with each channel.

In some embodiments, a coupling layer is disposed beneath the channel layer and is configured to be coupled reversibly to the thermal exchange layer.

In other embodiments, the cartridge includes an inlet and an outlet both in fluidic communication with at least one channel. In some embodiments, an integrated valve is in fluidic communication with each of the inlet and the outlet.

In yet other embodiments, the cartridge further includes one or more reagents (e.g., any described herein) on-chip.

In some embodiments, the miniature acoustic cell lysis device includes at least one channel formed in a microfluidic substrate, adapted to flow a fluid including biological cells therein; and an acoustic transducer having an operating frequency of greater than 10 MHz and preferably less than 100 MHz disposed on a lysis portion of each of the channels, adapted to propagate an acoustic wave in the fluid and thereby generating localized acoustic pressure to lyse the biological cells by acoustic pressure. The channel can further include a solid support (e.g., a filter) to capture the biological cells prior to release to the lysis portion of the channel.

The invention also features methods of lysing a cell in a test sample. The method can include introducing the test sample to at least one channel in a miniature acoustic cell lysis system (e.g., any described herein); providing a radiofrequency signal to at least one of the plurality of acoustic transducers, thereby generating localized acoustic pressure to lyse a cell by acoustic pressure and obtaining a lysate; and transporting the lysate through the channel.

In some embodiments, the method includes filtering the lysate to remove cellular debris and separate a target (e.g., a nucleic acid and/or a protein) within the sample.

In some embodiments, the sample (e.g., blood, plasma, serum, saliva, sputum, cerebral spine fluid, or urine) includes any useful cell, such as bacterial cells.

In some embodiments, the method includes acoustically focusing one or more cells within the test sample.

In some embodiments, the method includes stripping a sample including biological cells from a slide smear using a stripping buffer; pumping the sample-containing stripping buffer through a channel of the device, thereby capturing the biological cells on the filter; releasing the capturing biological cells from the filter using a rinse buffer; and lysing the biological cells in the rinse buffer in the lysing portion of the device, thereby releasing the cellular content from the biological cells. The rinse buffer can be static or flowing in the lysing portion during lysing. The released cellular content can include genomic material and/or un-denatured proteins.

In any of the embodiments herein, each acoustic transducer can be controlled separately and operated over a wide range of power settings for tailored operation.

In any of the embodiments herein, the system, device, or method encompasses rapid processing times, minimal sample consumption for higher throughput across larger sample sets, a portable footprint, ease of integration with other nanofluidic and/or microfluidic devices, beneficial release of undamaged proteins as well as nucleic acids for analysis, lack of a cooling system, and/or reusable or disposable components.

In any of the embodiments herein, the channel is a microchannel or a nanochannel.

In any embodiment herein, the operating frequency of at least one acoustic transducer (e.g., a lysing transducer) is of from about 50 MHz to about 100 MHz (e.g., from about 50 MHz to 80 MHz, 50 MHz to 90 MHz, 60 MHz to 80 MHz, 60 MHz to 90 MHz, 60 MHz to 100 MHz, 65 MHz to 80 MHz, 65 MHz to 90 MHz, 65 MHz to 100 MHz, 70 MHz to 80 MHz, 70 MHz to 90 MHz, or 70 MHz to 100 MHz).

In any embodiment herein, at least one acoustic transducer is a low frequency transducer.

In any embodiment herein, the operating frequency of at least one acoustic transducer (e.g., a focusing transducer) is of from about 0.5 MHz to about 10 MHz (e.g., from about 0.5 MHz to 2 MHz, 0.5 MHz to 5 MHz, 1 MHz to 2 MHz, 1 MHz to 5 MHz, 1 MHz to 10 MHz, 2 MHz to 5 MHz, 2 MHz to 10 MHz, or 5 MHz to 10 MHz).

DEFINITIONS

As used herein, the term "about" means+/−10% of any recited value. As used herein, this term modifies any recited value, range of values, or endpoints of one or more ranges.

By "disposed" is meant that a first structure is located in a particular position relative to a second structure. This position include direct contact between the first and second structures (e.g., direct continuous or noncontinuous contact) or indirect contact between the first and second structures (e.g., by way of third or further structure(s) disposed between the first and second structures).

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a cartridge, platform, platen, layer (e.g., thermal exchange layer or any layer described herein), and/or a substrate, which may or may not occur depending on the compositions of the substance and materials, does not constitute fluidic communication.

By "microfluidic" or "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm.

By "nanofluidic" or "nano" is meant having at least one dimension that is less than 1 µm. For instance, a nanofluidic structure (e.g., any structure described herein) can have a length, width, height, cross-sectional dimension, circumference, radius (e.g., external or internal radius), or diameter that is less than 1 µm.

As used herein, the terms "top," "bottom," "upper," "lower," "above," and "below" are used to provide a relative relationship between structures. The use of these terms does not indicate or require that a particular structure must be located at a particular location in the system.

Other features and advantages of the invention will be apparent from the following description and the claims.

DETAILED DESCRIPTION OF THE INVENTION

Most biosensors require a critical sample preparation procedure prior to detection of a target (e.g., a nucleic acid, a protein, etc., or any described herein). Depending on the type of biosensor, whether it is whole cell, genomic (DNA), or protein based, the problem is how to gain access to specific target biomolecules in a timely manner, while reducing the background to a low interference level. To solve this problem, the present invention uses high frequency acoustic waves that rapidly disrupt cellular membranes without chemical treatment, thereby releasing the intracellular material without damage or undesirable physical or chemical modification. Since the acoustic waves are applied remotely, the nano/microchannel device or cartridge can be discarded after use. In some embodiments, each transducer can be controlled separately and operated over a wide range of power settings for tailored operation. The system described herein is easily interfaced with existing nano/microfluidic and POC diagnostic technologies for the purpose of creating disposable, inexpensive, portable, and easy-to-use devices for global health and research applications.

Figure 1:
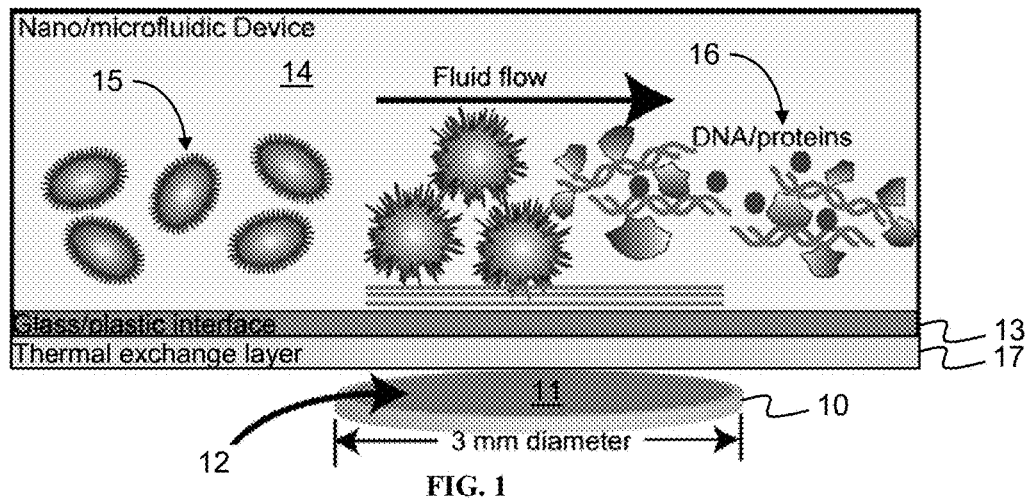
FIG. 1 is a schematic showing the principle of operation for acoustic lysis in a fluidic region 14 in a cartridge interfaced with an acoustic transducer 11 via a thermal exchange layer 17.

FIG. 1 shows the principle of operation of the miniature acoustic cell lysis system of the present invention. When an alternating voltage is applied across a piezoelectric transducer 10, the piezoelectric material is strained out-of-the plane, thereby defining the propagation direction. Optionally, the transducer 10 includes a top electrode 11 on the top surface and a bottom electrode (not shown) on the bottom surface. Electrodes can be placed in any useful configuration. In some instances, the device in FIGS. 1 and 2 uses parallel set electrodes, where each face of the transducer is metallized.

These longitudinal or compression waves 12 travel with a displacement parallel to the propagation direction and through a thermal exchange layer 17 and an interface 13 into adjoining media, here the fluid region 14 of the device. The thermal exchange layer 17 includes a material having high thermal conductivity and/or high thermal diffusivity, thereby facilitating heat transfer away from the sample.

The interface 13 can include glass, ceramic, thin plastic, or other low-loss acoustic materials, such as silicon. Therefore, the acoustic waves 12 easily penetrate into the fluid-filled region 14 of the cartridge. The acoustic waves 12 have sufficient energy to overcome the intermolecular bonding forces among biological cell enclosures, such as phospholipids, lipid proteins, and peptidoglycans of external and internal membranes for biological cells, including the cellular lipid bilayer membrane, the outer plasma membrane, and internal organelle membranes. Therefore, cells 15 entering the lysing portion of the fluid region 14 have their cellular membranes disrupted (lysed), releasing their internal contents 16, such as DNA and proteins, into the fluid for downstream processing and analysis.

The present invention relies on the piezoelectric effect to induce acoustic waves. The piezoelectric effect fundamentally describes the accumulation of charge in certain solid materials such as crystals, in response to applied mechanical stress. It is a reversible process where direct piezoelectricity occurs when electrical charges appear at the surface of a strained medium or, in this case, as the converse effect where a solid becomes strained when placed in an electric field. Piezoelectricity introduces linear coupling between the acoustic field equations and Maxwell's electromagnetic field equations. This provides the physical basis for all practical applications of acoustic fields, such as electrically generating and detecting acoustic vibrations. The nature of the piezoelectric effect depends on whether electric dipole moments can be induced as a result of asymmetry. The type of acoustic wave, velocity, and coupling strength depend on the material and its crystallographic orientation. Using these concepts, compression waves are generated within the transducer crystal and propagated into the fluid region of the POC device.

The nano/microfluidic or POC device may be fabricated from glass, thin plastic, or other low-loss acoustic materials, such as silicon. The acoustic waves easily penetrate into the fluid filled regions of the nano/microfluidic or POC device. We have tested the system using plastic cartridges designed to capture DNA using magnetic nanoparticles, filters, and electrostatic methods. This suggests that the technology is widely applicable for a range of nano/microfluidic devices in the market.

The present invention provides significant advantages over traditional methods. For instance, some bacterial cell walls contain complex lipids that significantly increase its resistance to disruption. Thus, it is difficult to obtain DNA from MTB using traditional methods. The acoustic waves generated by the present invention are substantially smaller and of higher frequency than other acoustic methods, allowing it to quickly disrupt lipid membranes and cell walls using minimal power with no cooling requirements.

In addition, energy transfer in the present invention is more efficient and requires far less power to achieve the same level of lysis efficiency as lower frequency (20-40 kHz) commercial systems (Cooley E J et al., "A versatile DNA extraction system for rapid sample preparation using acoustic lysis," *Biomed. Eng. Soc.* (BMES) conference held on Oct. 4, 2008 in St. Louis, Mo. (1 page)). For example, for a transducer centered at 68 MHz, the acoustic wavelength in the fluid (22 µm) is very similar to the size of biological cells (approximate range of 2 to 30 µm). Further, the operating frequency is preferably less than 300 MHz and more preferably less than 100 MHz to enable efficient coupling into the fluid. Further, unlike commercial acoustic transducers, the miniature transducer does not generate significant amounts of heat, making it compatible with protein assays. Finally, the acoustic lysis method avoids costly time changing procedures and sample preparation delays each time the biological agent is changed.

As described herein, the system and lysing methods employ a cartridge for handling test samples and a platform providing an array of acoustic transducers. In some embodiments, a thermal exchange layer is disposed between the cartridge and the platform, where this layer can be affixed to the cartridge and/or the platform or else provided as a detached component configured to remain between the cartridge and platform in operation. Additional details follow.

Cartridge

The present invention encompasses a system and a method having a cartridge for handling test samples. Such cartridges can optionally include one or more reagents for detecting targets within the test sample (e.g., any reagent described herein). In particular, the cartridge contains and transports the test sample to enable sample preparation, such as a lysing step.

To facilitate fluid transport, the cartridge can have one or more channels (e.g., nanofluidic and/or microfluidic channels). The channel can have any useful dimension, such as length, width, height, or cross-section (e.g., rectangular, circular, ellipsoid, triangular, etc.). In addition, any of these dimensions can be uniform (e.g., straight, curved, serpentine, etc.) or variable (e.g., tapered, widened, branched, etc.) along its length. In particular, the cartridge includes an array of channels in any useful format (e.g., a format including a parallel array of channels having a main channel branching into a plurality of channels or an array having a plurality of channels converging into a main channel).

Figure 2:
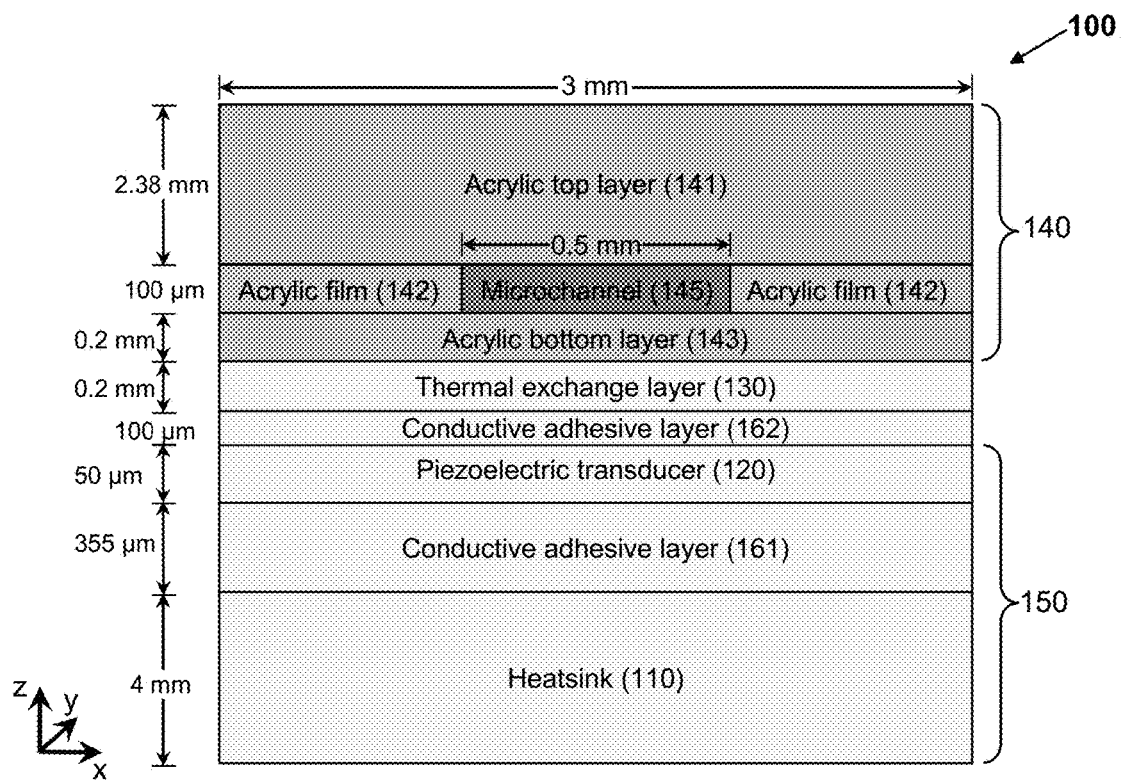
FIG. 2 is a cross-sectional schematic of a portion of an exemplary acoustic lysis system 100 having a microchannel 145, a thermal exchange layer 130, and an acoustic transducer 120.

Exemplary cartridges are provided in FIGS. 2 and 3A-3D. FIG. 2 shows a cross-sectional end-view illustration of an exemplary system 100 having a cartridge 140 and a platform 150 having a bulk acoustic wave (BAW) transducer 120. The cartridge structure was modeled using a 1D transmission line model and finite element modeling, as described in U.S. patent application Ser. No. 12/872,919, filed Aug. 31, 2010, which is incorporated herein by reference in its entirety. In this non-limiting example, the cartridge 140 includes a 0.5 mm wide×100 μm high channel 145 formed in a 100 μm thick acrylic film 142 sandwiched between a 0.2 mm thick acrylic bottom layer 143 and a 2.38 mm thick acrylic top layer 141. Alternatively, the cartridge can be formed within a single layer with a channel formed thereof or multiple layers (e.g., two or more layers) having a channel formed within and/or between the layers. Furthermore, the cartridge can be formed from acrylic or any other useful material (e.g., any polymer or plastic described herein).

Figure 3A:
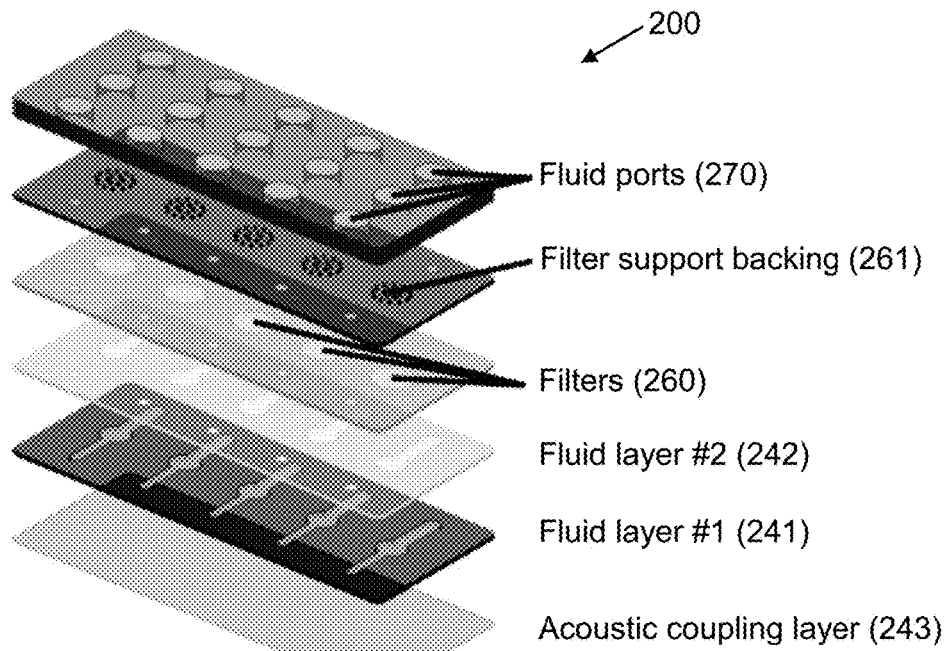
FIG. 3A-3E shows an exemplary acoustic lysis cartridge 200. Provided are different perspective of the cartridge: (A) an exploded view showing multiple layers, (B) a plan view showing five microchannel elements 205, (C) a close-up view of element 205 having microchannel 245, and (D) a cross-sectional view of the element 205 along line marked D in FIG. 3B. Also shown is (E) a schematic of the cartridge 200 in use with a cell sample.

As shown in FIG. 3A, an exemplary cartridge structure 200 can include multiple layers. These layers include a plastic acoustic coupling layer 243, two microchannel fluid layers 241, 242, a filter layer 260, a filter support backing layer 261, and a top layer 270 including the fluidic ports and O-ring seals. For example, the cartridge can be a laminated acrylic cartridge. Microchannel features can be cut in a thin cast acrylic sheet (e.g., 100 μm) using a $CO_2$ laser. The acrylic layers can be bonded together using acrylic-based solvents under pressure to create water tight seals between the layers.

Figure 3B:
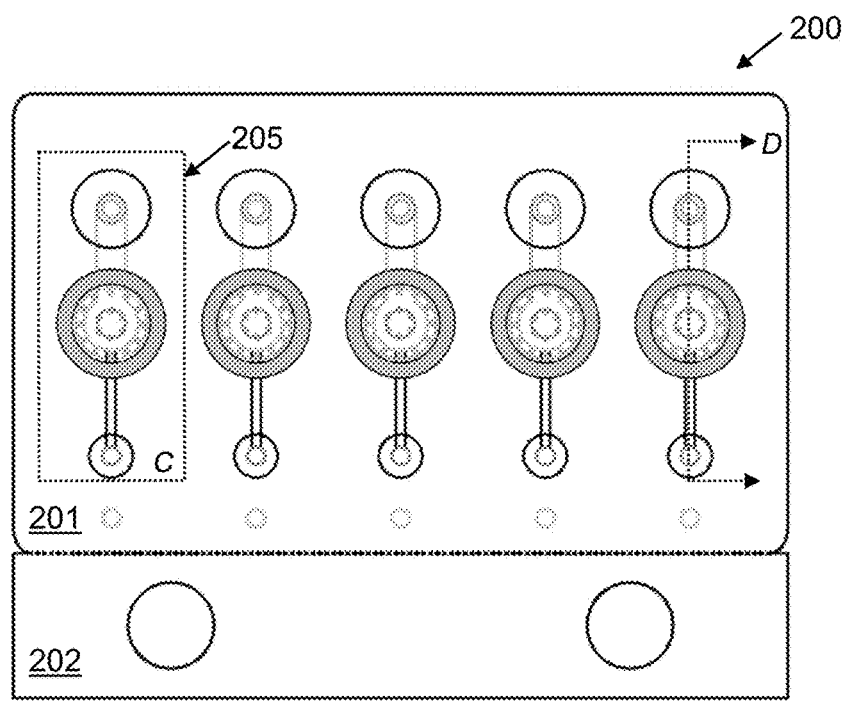
Figure 3C:
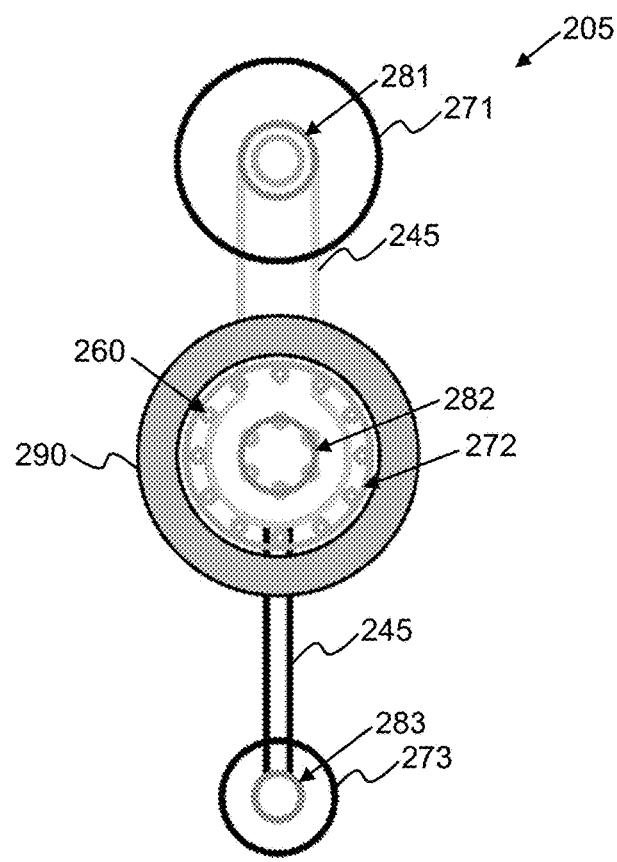

FIG. 3B shows a top-view illustration of a 5-channel disposable cartridge 200 that can be used for parallel lysis applications. The multiple channels can be combined together or used separately to build more complex biological processing operations, such as fluid mixing. This cartridge 200 has five independent lysing element 205 per die 201. In each element, raw sample can be introduced into a fluidic port and flowed over a single bulk acoustic wave transducer and the lysate exits the lysing channel. The bottom section 202 serves as a break-away portion for layer alignment. FIG. 3C shows a magnified view of a lysing element 205, which includes a lysing channel 245, an inlet 281 to the channel 245, a sample port 271 in fluidic communication with the inlet 281, an outlet 283 to the channel 245, and an exit port 273 in fluidic communication with the outlet 283. The sample and exit ports 271, 273 can optionally include a valve or a gasket.

The cartridge 200 can further include a filter 260 for capturing and concentrating the biological cells or targets prior to being lysed. The lysing element 205 can include a filter 260 in fluidic communication with the lysing channel 245. One or more inlets/outlets 282 can be included to either withdraw filtered material (e.g., a filtrate, a waste product, etc.) from the channel 245 or to inject one or more reagents through the filter 260. The cartridge can include a port 272 and an o-ring gasket 290 in fluidic communication with the inlet/outlet 282. For instance, stripping buffers and rinse buffers can be removed or introduced through a waste port 282 during collection and release of the cells from the filter 260. The cartridge can further provide the necessary fluidics to mix the lysate with a nucleic acid extraction portion downstream (not shown) from the acoustic lysing portion.

To extract nucleic acid from the lysed sample, the device can use several integrated approaches (e.g., such as magnetic beads, electrostatic capture, or filtration methods, as described in U.S. patent application Ser. No. 12/872,919). Any of the surfaces of the cartridge can include one or more coatings (e.g., to minimize adsorption of one or more cells, proteins, nucleic acid, reagents, and/or chemical agents). Exemplary coatings include polyethylene glycol, a perfluorinated polymer (e.g., Teflon®, polytetrafluoroethylene), a protein (e.g., a serum protein such as human or bovine serum albumin, or an extracellular matrix protein such as fibronectin), a gel (e.g., a hydrogel), a silane, a polymer (e.g., Parylene™, a poly(p-xylylene)-based polymer), an insulator (e.g., screen-printed polymers, epoxies, ceramics, and the like), etc.

Similarly, inert polymer coatings, Parylene™ coatings, or surface silanation modifications may also be applied to internal surfaces of the cartridge in order to make the overall system more compatible with the reactions being carried out. For example, in the case of nucleic acid analysis, it may be desirable to coat the surfaces with, e.g., a non-stick coating to prevent adhesion of nucleic acids to the surface. Additionally, patterned metal electrical conductors for activating actuators, heaters, sensors, and the like may be used. Such conductors may be coated with insulator coatings in those instances where electrical leads are placed in contact with fluids, to prevent shorting out or gas formation from electrolysis.

The cartridge can be formed from any useful material. Exemplary materials include a polymer, such as an acrylic polymer (e.g., a polymer formed from acrylic acid alkylester (e.g., ethyl or butyl ester), butyl acrylate, butyl methacrylate, 2-chloroethyl vinyl ether, ethyl acrylate, 2-ethylhexyl acrylate, hydroxyethyl methacrylate, methyl acrylate, methacrylate, and/or trimethylolpropane triacrylate, or copolymer thereof), polymethyl methacrylate (PMMA), polyethylene terephthalate (PET, e.g., biaxially-oriented PET or bo-PET), polybutylene terephthalate (PBT), poly(dimethylsiloxane) (PDMS), polycarbonate (PC), cyclo-olefin copolymer (COC), polyethylene terephthalate glycol (PETG), polyethylene (PE, such as branched homo-polymer PE), polyvinylchloride (PVC), polystyrene (PS), styrene copolymer, polyimide (PI), polypropylene (PP), polytetrafluoroethylene (PTFE), polynorbornene (PN), poly(4-methyl-1-pentene), silicone, and combinations or co-polymers thereof; plastic (e.g., including any polymer described herein); silicon; glass; ceramic; an adhesive, such as any described herein; as well as combinations thereof (e.g., combinations of such materials provided in separate layers or within the same layer). Polymers can include any useful additive, such as, e.g., fillers (e.g., mica, talc, or calcium carbonate), plasticizers (e.g., dioctyl phthalate), heat stabilizers (e.g., organotin compounds), antioxidants (e.g., phenols or amines), and/or UV stabilizers (e.g., benzophenones or salicylates). Such materials can be provided in any useful form, such as in one or more layers that can be laminated to provide the assembled cartridge.

The cartridge can be fabricated by employing any useful technique. Exemplary methods of fabrication include bulk or surface micromachining, microfabrication (e.g., by casting, injection molding, compression molding, embossing, ablation, thin-film deposition, and/or Computer Numerically Controlled (CNC) micromachining), rapid prototyping, photolithography, and etching techniques (e.g., wet chemical etching, reactive ion etching, inductively coupled plasma deep silicon etching, laser ablation, or air abrasion techniques).

In particularly preferred embodiments, the cartridge is made from at least one injection molded, press molded or machined polymeric part that has one or more chambers or depressions manufactured into its surface to define several of the walls or channels of the fluidic regions. Examples of suitable polymers for injection molding or machining include, e.g., polycarbonate, polystyrene, polypropylene, polyethylene, acrylic, and commercial polymers, such as Kapton™ (a polyimide), Valox™ (a PBT and/or PET resin), Teflon™ (PTFE), acrylonitrile butadiene styrene (ABS), Delrin™, and the like. A second part that is complementary in shape is mated to the surface of the first part to define the remaining wall of the cartridge. The mating part or a third part may be a printed circuit board for implementing electrical contact directly with the fluid or indirectly via the cartridge.

In another instance, the cartridge can include multiple layers bonded together with embossing, laminating, and/or bonding techniques. In some instances, one or more layers can include use of an adhesive. Exemplary adhesives include a pressure sensitive adhesive (e.g., an acrylic, silicon, or acrylic-hybrid based adhesive optionally including a support layer), a polyethylene terephthalate adhesive (e.g., biaxially-oriented polyethylene terephthalate (bo-PET), often marketed as Mylar™), an acrylic adhesive, an acrylic-hybrid adhesive, a silicone adhesive, and/or an adhesion promoter (e.g., Dow Corning® 1200 primer, including light aliphatic petroleum solvent naptha, xylene, tetrapropyl orthosilicate, tetrabutyl titanate, ethylene glycol methyl ether, tetra (2-methoxyethoxy) silane, and/or ethylenbenzene).

The cartridge may also incorporate one or more solid supports (e.g., one or more filters) for capturing sample components, e.g., RNA, DNA, proteins, cells, spores, or microorganisms to be lysed. The solid support may also be used for removing particulates, cell debris, and protein solids from the sample. The solid support may be within any region, e.g., within the fluid passages or channels leading between regions or within a particular fluidic region. A variety of solid supports may be used, including, e.g., cellulose, nitrocellulose, polysulfone, nylon, vinyl copolymers, glass fiber, micromachined structures, and the like. Similarly, separation media, e.g., ion exchange resins, affinity resins or the like, may be included within the cartridge.

Any useful design consideration can be assessed to optimize the cartridge of the invention. For example, cartridges fabricated in plastic offer a much simpler path toward a disposable cartridge assembly. In another example (e.g., in FIG. 3D), the bottom layer 244 that separates the fluidic region 245 from the transducer 220 is preferably thin or of a rigid material to minimize acoustic loss. Though glass has lower acoustic loss than plastic, a sufficiently thin plastic layer (i.e., about 25 µm) can perform as well as thicker glass layers.

In yet another example, the height of the channel is preferably comparable to the acoustic attenuation length in the fluid and depends on the excited wavelength for optimal propagation distance. Preferably, the acoustic wavelength in the fluid is comparable to the size of the cells to be lysed (e.g., an acoustic wavelength of from about 10 µm to 30 µm, e.g., from 15 µm to 30 µm, 20 µm to 30 µm, or 25 µm to 30 µm). For example, the height of the channel can preferably be less than ten acoustic wavelengths in the fluid and, more preferably, less than a few acoustic wavelengths (e.g., a channel height of from about 15 µm to 300 µm, e.g., from 15 µm to 50 µm, 15 µm to 100 µm, 15 µm to 150 µm, 15 µm to 200 µm, 15 µm to 250 µm, 50 µm to 100 µm, 50 µm to 150 µm, 50 µm to 200 µm, 50 µm to 250 µm, 50 µm to 300 µm, 100 µm to 150 µm, 100 µm to 200 µm, 100 µm to 250 µm, 100 µm to 300 µm, 150 µm to 200 µm, 150 µm to 250 µm, 150 µm to 300 µm, 200 µm to 250 µm, or 200 µm to 300 µm).

In one example, the width of the channel is preferably smaller than the acoustic transducer to maintain lysing uniformity. However, the width of the channel is preferably large enough to minimize pressure drop through the cartridge thereby avoid excessive back pressure.

In yet another example, the channel length can be short to minimize pressure drop and to reduce biological loss to the channel walls.

The present cartridge can include one or more channels or chambers (e.g., a substantially enclosed region or volume having one or more inlets and/or outlets), which can be designated for a particular use. Optionally, the chamber can have one or more reagents (e.g., any described herein). Particular uses for such channels and chambers include a sample channel/chamber for receiving and/or storing a test sample, a lysing channel/chamber disposed above an acoustic transducer to facilitate lysis for a sample in that channel/chamber, an incubation chamber for incubating a test sample, a reagent chamber containing one or more reagents for detecting one or more targets, a sterilization chamber containing one or more reagents to sterilize or disinfect the test sample (e.g., containing one or more sterilization agents, as described herein), an assay chamber for conducting one or more assays to detect one or more targets (e.g., an assay chamber containing a PCR assay), and/or a waste chamber for storing one or more by-products of the assay. Each of these chambers can be interconnected by a fluidic connector and/or a channel that can optionally include a valve in its fluidic path. Alternatively, one or more channels or chambers can be provided in one or more separate cartridges, where one or more fluidic connectors connect the cartridges. For instance, the system can include a lysing cartridge having a lysing channel, a reagent cartridge having a reagent channel, and an assay chamber for PCR analysis, where the lysing cartridge is in fluidic communication with the reagent cartridge, which in turn is in fluidic communication with the assay cartridge. In some cases, chambers in the cartridge may be used as a volumetric region, e.g., to precisely measure fluid volumes for introduction into an adjacent region. In such cases, the volume of the chamber is dictated by volumetric needs of a given reaction. Further, the cartridge may be fabricated to include a series of chambers having varied dimensions and volumes in comparison to each other.

The cartridge can include one or more fluidic connecters to facilitate entry of a sample, a reagent, a by-product, or a chemical into and out of the cartridge. Exemplary fluidic connectors include one or more inlets, outlets, gaskets (e.g., o-rings), seals, valves, ports (e.g., a sample port that receives the test sample), vents, plugs, tubing, pipes, ducts, and/or side channels.

Thermal Exchange Layer

The present invention encompasses systems and methods employing a thermal exchange layer. In particular, this layer facilitates removal of heat that could accumulate during operation of the acoustic transducer(s).

The thermal exchange layer is disposed between the cartridge and the platform. As shown in FIG. 2, the thermal exchange layer 130 can be affixed to the cartridge 140 or to the platform 150. In one embodiment, if the cartridge is to be disposed after a single use, then the thermal exchange layer can be conserved by affixing this layer to the platform.

Alternatively, the thermal exchange layer can be a detached layer that is disposed between the cartridge and the platform. In this embodiment, the thermal exchange layer can be mechanically coupled between the cartridge and platform by pressure applied by the platen (e.g., as described herein).

For the exemplary system in FIG. 2, the topside of a 0.2 mm thick aluminum nitride (AlN) thermal exchange layer 130 is mechanically and reversibly coupled to the cartridge structure 140. A one-micron gold top electrode pattern can be defined on the backside surface of the AlN layer 130. A transducer layer 120 (e.g., a 36°Y lithium niobate layer having a thickness of about 50 μm and a diameter of about 3 mm) can be bonded to the gold-patterned backside of the AlN layer 130 using a thin conductive adhesive layer 162 (e.g., 100 μm of conductive epoxy). A voltage can be applied between the top and bottom electrodes to energize the piezoelectric transducer. The transducer is capable of several power settings ranging from gentle mixing to cell membrane disruption (lysis). The transducer layer 120 and the AlN layer 130 can then be encapsulated, leaving an opening on the backside of the piezoelectric transducer.

The backside opening can then be backfilled with a thicker conductive adhesive layer 161 (e.g., 355 μm of conductive epoxy), which electrically connects the transducer 120 to an electrical node and thermally to a heat sink 110 (e.g., an aluminum heatsink layer having a thickness of about 4 mm). Exemplary conductive adhesives for the conductive adhesive layers 161, 162 include a conductive material (e.g., silver, gold, copper, or graphite) in a base (e.g., a resin, an epoxy, an acrylate, a cellulose, a solvent, an elastomer, a polyester, or a polymer), such as those available as Epo-tek® E4110 (an electrically conductive, silver-filled epoxy paste) from Epoxy Technology, Inc., Billerica, Mass. In addition, one or more conductive adhesive layers can be used to pattern, adhere, or encapsulate the transducer(s), support layer(s), thermal exchange layer(s), and/or heatsink layer(s).

In particular, the heatsink and/or thermal exchange layer facilitates removing heat from the target. For instance, the heat sink can remove heat from the lysing region and the acoustic transducers. In another instance, the heat sink and the thermal exchange layer dramatically reduces sample heating, which is critical to preserving the conformation of DNA and preventing denaturing proteins. Indeed, the temperature rise can be only 4° C. above ambient after 30 seconds of lysing treatment.

The thermal exchange material can be formed from any useful material. Exemplary materials include aluminum nitride, silicon carbide, silicon nitride, boron nitride, beryllium oxide, copper, silver, gold, graphene, diamond, a thermal epoxy (e.g., a conductive epoxy including an epoxy resin (e.g., a bisphenol A epoxy resin), a curing agent or hardener, and one or more particles of a conductive material, such as silver, nickel, graphite, steel, etc.), stainless steel, or composites thereof. Other materials include any having high thermal conductivity (e.g., a thermal conductivity of about 150 W/m·K or greater) and/or high thermal diffusivity (e.g., a thermal diffusivity of $3.14 \times 10^{-6}$ m$^2$/s or greater) to reduce internal heat accumulation. The thermal exchange material can be further processed, such as by dicing, firing, annealing, hot pressing, etc.

Solid Support

Following lysis, it will often be desirable to separate the target cellular components (e.g., nucleic acids or proteins) from other elements of the crude extract, e.g., denatured proteins, cell membrane particles, and salts. Removal of particulate matter is generally accomplished by filtration, flocculation and the like. A variety of filter types may be readily incorporated into the fluidic regions of the cartridge. Further, where chemical denaturing methods are used, it may be desirable to desalt the sample prior to proceeding to the next step. Desalting of the sample and isolation of the nucleic acid may be carried out, e.g., by binding the nucleic acids to a solid phase and washing away the contaminating salts, or by performing gel filtration chromatography on the sample, by passing salts through dialysis membranes, and the like. Suitable solid supports for nucleic acid binding include, e.g., filters, beads, fibers, membranes, glass wool, filter paper, polymers, and gel exclusion media.

In some embodiments, enzymes may be coupled to a suitable solid support (e.g., agarose, cellulose, silica, divinylbenzene, polystyrene, etc., or any desired herein). Coupling of enzymes (e.g., polymerases or monoclonal antibodies) to solid supports can impart stability to the enzyme, thereby allowing for long-term storage (e.g., for days, weeks or months). Any useful linker (e.g., an alkylene group, a poly(ethylene glycol), a peptide chain, etc.) can be used to attach the enzyme to the support.

The cartridge can include one or more filters to capture a target (e.g., target DNA, RNA, or proteins), to remove cellular debris, and/or to recover one or more targets in the filtrate. Exemplary filters include one or more hydrophilic filters (e.g., a polyvinylidene fluoride (PVDF) or polypropylene filter), hydrophobic filters (e.g., a polytetrafluoroethylene (PTFE) filter), glass fiber membranes, nylon membranes, cellulose membranes (e.g., regenerated cellulose or cellulose ester membranes), polyethersulfone (PES) membranes, etc. In one instance, the filter can be fabricated from hydrophilic PVDF membrane or other suitable micropore filter material. For example, a membrane about 125 μm thick with a 0.45 μm pore size can have a water flow rate of about 29 ml/min/cm$^2$. Assuming a bacterial diameter of 0.4 μm, the filter can capture $5.2 \times 10^7$ bacteria for the closest packed layer case. Multiple filter layers can also be used.

Valves

The present systems can also include one or more valves (e.g., integrated valves). A significant challenge in this work is to reduce biological losses in the cartridge from both cell loss and DNA loss in the cartridge. In some cases, passivation of the plastic cartridge (e.g., with one or more coatings described herein) is suitable if the fluid stays within the cartridge and has limited off-chip processing. Another source of biological loss could be due to the locating valves off-cartridge. Accordingly, the present invention encompasses cartridges having one or more valves that minimize sample and/or target loss. Exemplary valves include a diaphragm-based isolation valve (e.g., a Liquid-X® valve, such as LQX12 available from Parker Hannifin Corp., Hollis, N.H.), a solenoid valve (e.g., an LFYA valve, such as a 2-Way 156 MINSTAC Style available from Lee Co., Westbrook, Conn.), a proportional valve, a pilot valve, and/or a pneumatic solenoid valve, including any of these valves integrated within the cartridge (e.g., in one or more inlets, outlets, or ports).

Platform and Platen

The present system employs a platform having one or more acoustic transducers. In particular embodiments, each acoustic transducer is disposed on a transducer array substrate that is reversibly mechanically coupled to a cartridge. The transducer array substrate can include any useful material (e.g., aluminum nitride or fused silica).

The platform can include a plurality of transducers, where each transducer is configured to be disposed beneath a lysing channel in the cartridge. For instance, as shown in FIG.

3A-3B, the cartridge 200 can include five lysing elements 205, and the platform can then include five acoustic transducer, where each transducer is located beneath each lysing element 205 (e.g., a circular transducer located beneath the portion of the channel underlying each filter 260).

Figure 5A:
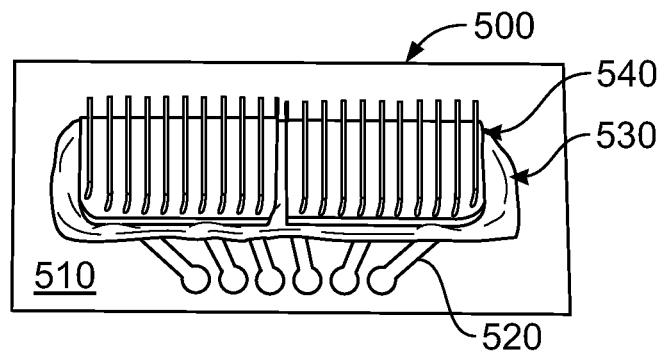
FIG. 5A-5B shows an exemplary platform for operating the cartridge. Shown are (A) a photograph of a transducer array 500 having five transducers on an aluminum nitride thermal exchange layer and with an aluminum heat sink and (B) a photograph of a radiofrequency (RF) driver board 550 to drive the transducer array.
Figure 5B:
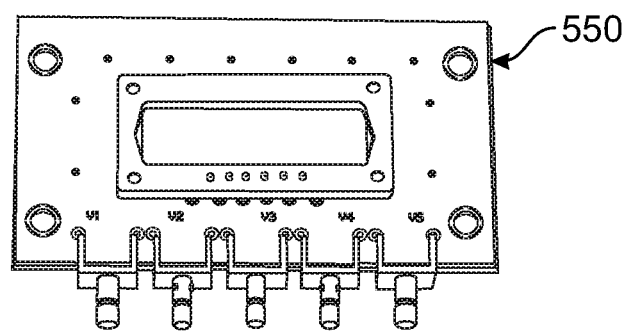

An exemplary platform is provided in FIG. 5A-5B. As can be seen, the platform 500 includes a substrate 510 and an array of electrodes 520, where each electrode is connected to a transducer located beneath the conductive adhesive 530 and the aluminum heatsink 540. The platform can also include a RF driver board 550 configured to electrically connect to the electrode 520, thereby driving the transducer. The RF driver board can be electrically connected to an RF circuit within the platform. For example, the RF circuit can include a tunable RF source (e.g., a source ranging from about 60 to 80 MHz); a controller electrically connected to the RF source to tune this source; and a RF power amplifier electrically connected to the RF source (e.g., a 2 W fixed amplifier, such as Model No. ZHL-1-2 W-S available from Mini-Circuits, Brooklyn, N.Y.). Optionally, the RF circuit includes one or more power splitters electrically connected to the amplifier, where each splitter in turn is electrically connected to a transducer (e.g., by way of a contact pad on the electrode electrically connected to that transducer).

Figure 6A:
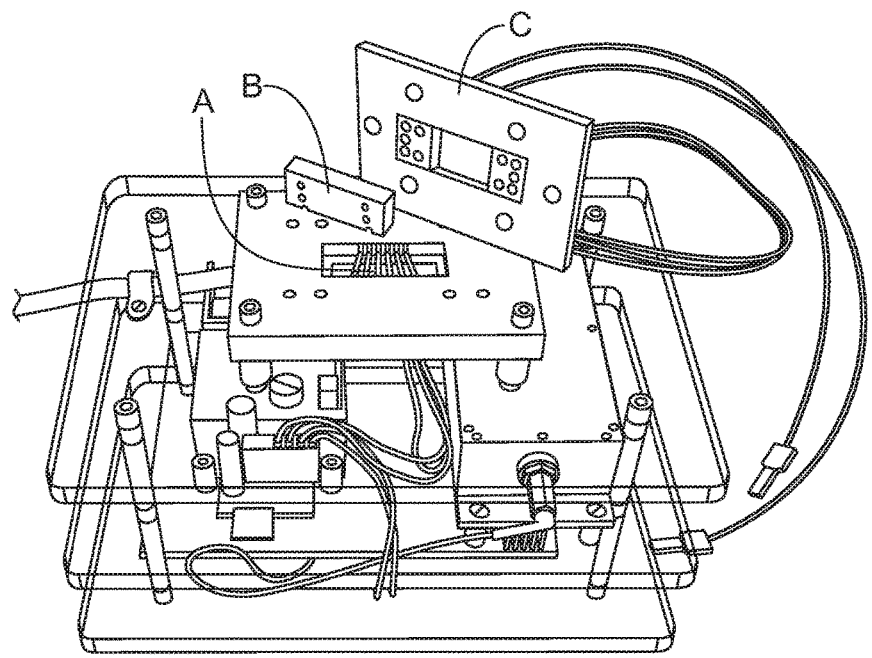
FIG. 6A-6B shows an exemplary system including a disposable and removable cartridge for use with a platform having a transducer array. Shown is (A) a photograph of the system having a platform (labeled A) with a five channel acoustic transducer array that couples reversibly to the user-specified cartridge (labeled B). A platen (labeled C) holds the nano/microfluidic cartridge in contact with the acoustic array, while also providing fluidic connections. The acoustic transducers and associated channels can be combined together or used separately to build more complex biological processing operations, such as fluid mixing. Also shown is (B) a photograph of various cartridges for use with the platform, including (A) a five-channel lysis cartridge with filter-based DNA extraction for *M. tuberculosis* (MTB), (B) a single-channel lysis cartridge with electrostatic DNA extraction employing coated electrodes, (C) a multi-channel lysis cartridge, and (D) a single-channel lysis cartridge with mixing and magnetic bead DNA extraction.

The system can also include a platen, which provides mechanical contact between the cartridge and the platform. This contact can be reversible. In addition, the platen can be configured to provide one or more fluidic connectors (e.g., valves, tubing, etc.) that interface with the inlets, outlets, and/or ports of the cartridge. With this configuration, the platen provides a streamlined way to inject, transport, and receive fluid into and out of the cartridge. For instance, the platen can provide fluidic communication between an off-chip pumping system (e.g., any described herein) and the cartridge or between two separate cartridges. An exemplary platen is shown in FIG. 6A (labeled C).

Acoustic Transducer

The platform includes one or more acoustic transducers to provide a compression wave for lysis. Generally, the transducer includes a piezoelectric material or piezoelectric crystal. Such materials and crystals are characterized by a linear coupling between electrical and mechanical states. Thus, an applied electrical charge induces internal mechanical strain in the material, and, conversely, an applied mechanical strain generates internal electrical charge. These mechanical forces are delivered to the sample in the form of acoustic waves.

The characteristics of the acoustic wave depend on the type and crystal orientation of the transducer material. Exemplary materials include lithium niobate ($LiNbO_3$, e.g., 36°Y-cut $LiNbO_3$), potassium niobate ($KNbO_3$), lithium tantalate ($LiTaO_3$, e.g., 36°YX-cut $LiTaO_3$), quartz ($SiO_2$), lanthanum gallium silicate, lead zirconate titanate (Pb(Zr, Ti)$O_3$ or PZT, e.g., PZT-5H), polycrystalline lead titanate ($PbTiO_3$), PZN-PT, ceramics (e.g., $Pb(Mg_{1/3}Nb_{2/3})O_3$—$PbTiO_3$ (PMN-PT), barium titanate ($BaTiO_3$), lead zirconate-lead titanate ($[PbZr_xTi_{1-x}O_3]$-PZT), and lead titanate ($PbTiO_3$, PCT)), as well as single crystals, composites, laminates, and stacks thereof. Additional materials are provided in Shung K K et al., "Piezoelectric materials for high frequency medical imaging applications: a review," *J. Electroceram.* 2007; 19:139-45, which is incorporated herein by reference in its entirety.

Each acoustic transducer can have any useful dimension (e.g., length, width, height, thickness t, or cross-section), geometry (e.g., rectangular or triangular patches, disks, cones, cylinders, spheres, annuli, tubes, rods, pillars, etc.), and/or crystal orientation (e.g., an orientation that provides longitudinal or quasi-longitudinal waves, such as a 36° or 10° rotated Y-cut or Z lithium niobate). Furthermore, when transducers are provided in an array, each transducer in the array can be the same or different. For instance, to effect both acoustic focusing and lysing, the array can include one or more transducers having thickness $t_1$ for focusing and other transducer(s) having thickness $t_2$ for lysing, where $t_1 > t_2$.

Any useful acoustic transducer, as well as arrays thereof, can be included in the platform. For instance, the array can include a plurality of transducers, where each transducer is configured to be disposed beneath a lysing channel in the cartridge. Alternatively, a portion of the transducers can be dedicated to acoustic lysing, and another portion for other uses (e.g., mixing, microcentrifuging, injecting, assaying, pumping, etc.). In some embodiments, the transducer is capable of several power settings ranging from gentle mixing to cell membrane lysis.

To minimize cavitation (i.e., rapid formation and collapse of bubbles in a fluid), each transducer can be configured to deliver less than about 240 mW (e.g., to deliver from about 10 mW to about 240 mW, such as from 10 mW to 200 mW, 10 mW to 150 mW, 10 mW to 100 mW, 10 mW to 60 mW, 10 mW to 50 mW, 10 mW to 40 mW, 10 mW to 20 mW, 20 mW to 240 mW, 20 mW to 200 mW, 20 mW to 150 mW, 20 mW to 100 mW, 20 mW to 60 mW, 20 mW to 50 mW, 20 mW to 40 mW, 40 mW to 240 mW, 40 mW to 200 mW, 40 mW to 150 mW, 40 mW to 100 mW, 40 mW to 60 mW, or 40 mW to 50 mW).

The transducer can have one or more electrodes or contact pads providing electrical energy. For instance, the transducer can include a top electrode and a bottom electrode to energize the piezoelectric transducer. Referring to FIG. 2, the top electrode can be disposed between conductive adhesive layer 162 and transducer 120, and the bottom electrode can be disposed between the transducer 120 and the conductive adhesive layer 161. Optionally, a contact pad can be disposed on the top surface of a transducer substrate to provide electrical connection to the bottom electrode of the transducer (e.g., on transducer substrate 510 in FIG. 5A). The electrode(s) can be formed from any useful material (e.g., gold, chrome, silver, titanium, aluminum, nickel, palladium, platinum, and combinations thereof) and any useful technique (e.g., vacuum deposition, electroless depositions, etc.).

Acoustic Wave Lysis System

The present invention includes acoustic wave lysis systems having a cartridge and a platform, as described herein.

Figure 3D:
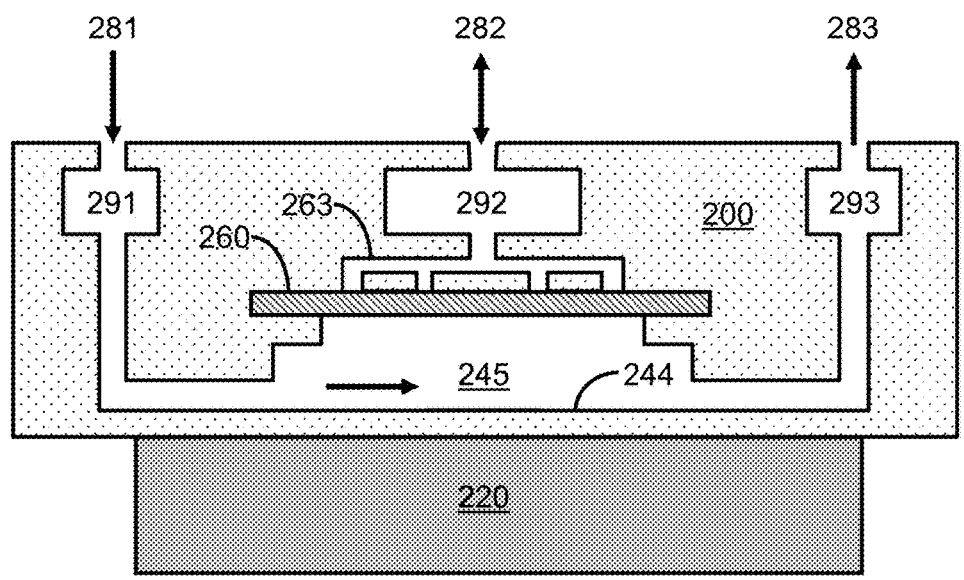

An exemplary system is provided in FIG. 3D. Here, a miniature acoustic cell lysis system is used for biological cell lysis by localized acoustic pressure. The lysing system includes a high-frequency bulk acoustic wave (BAW) transducer 220 mechanically and reversibly coupled to a disposable microfluidic cartridge 200 having a channel 245 formed therethrough. Reversible mechanical coupling of the cartridge 200 to the BAW transducer 220 enables reuse of the transducer assembly 220 while permitting disposal of the contaminated cartridge 200 after cell lysis. Alternatively, the transducer can be monolithically integrated with the microfluidic channel on the same substrate. As described herein, the system can include a heat sink and/or a thermal exchange layer to minimize sample heating.

Whole cells enter the channel 291 through an inlet 281. The whole cells can then flow through and be disrupted in a lysing portion of the channel 245 by acoustic pressure generated by the proximate transducer 220. Optionally, the bottom layer 244 that separates the fluidic region 245 from the transducer 220 is preferably thin, composed of a thermal exchange material, and/or includes a rigid material to minimize acoustic loss. Lysate containing the acoustically lysed cells can exit the channel 245 through an outlet 283. The cartridge 200 includes a filter 260 and a filter support structure 263 including one or more channels. Through inlet/outlet 282 in fluidic communication with filter 260, filtrate can be removed or a reagent can be injected into the channel 245. Connection regions 291, 292, 293 can include one or more seals to connect the inlet/outlet of the cartridge to a pumping system.

Figure 6B:
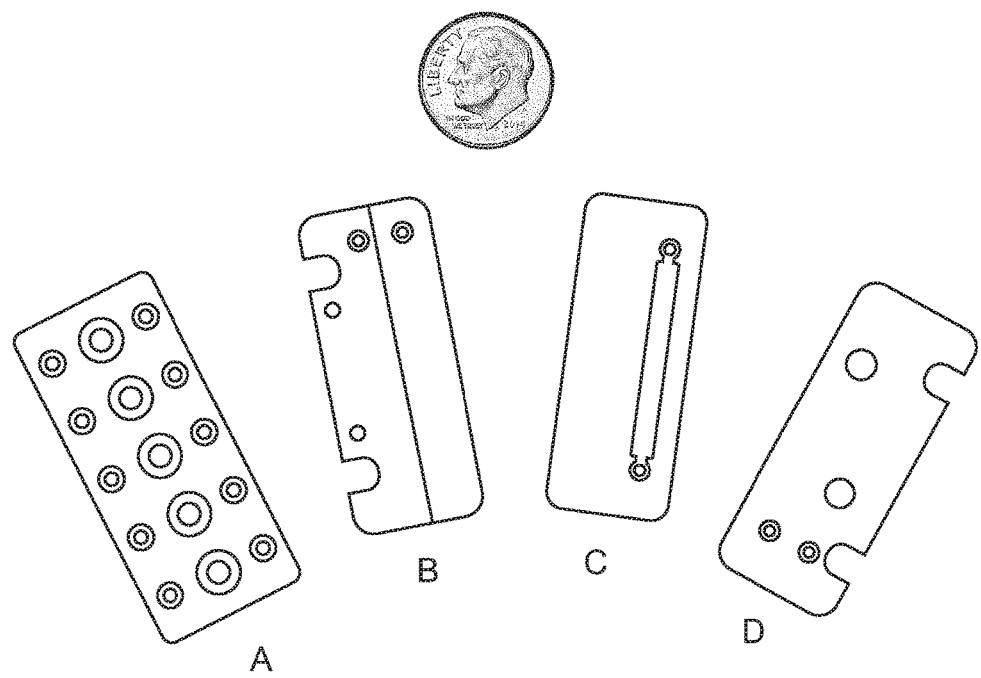

Photographs of an exemplary system are provided in FIG. 6A-6B. As can be seen in FIG. 6A, the system includes a platform (labeled A), a cartridge (labeled B), and a platen (labeled C). Due to the universal fitting between the cartridge and the platform/platen combination, cartridges having varied architecture can be interfaced with the platform and the platen. For instance, FIG. 6B shows various types of cartridges for use with the system. In particular, such a system could employ disposable cartridges formed from cost-effective plastic materials and a reusable platform and platen formed from costlier electronic, transducer, and metal components.

Any useful pumping system can be employed with the cartridge and platform of the invention. The pumping system can include one or more of the following: a high-throughput autosampler, a micropump, a distribution pump, a peristaltic pump, a syringe pump, a pressure pump, an electro-osmotic pump, a piezoelectric pump, a multichannel pump (e.g., a multichannel format of any pump described herein), a multicolumn compartment, and one or more fluidic connectors (e.g., any described herein, such as valves, tubing, etc.) to connect any component in the system.

Figure 7:
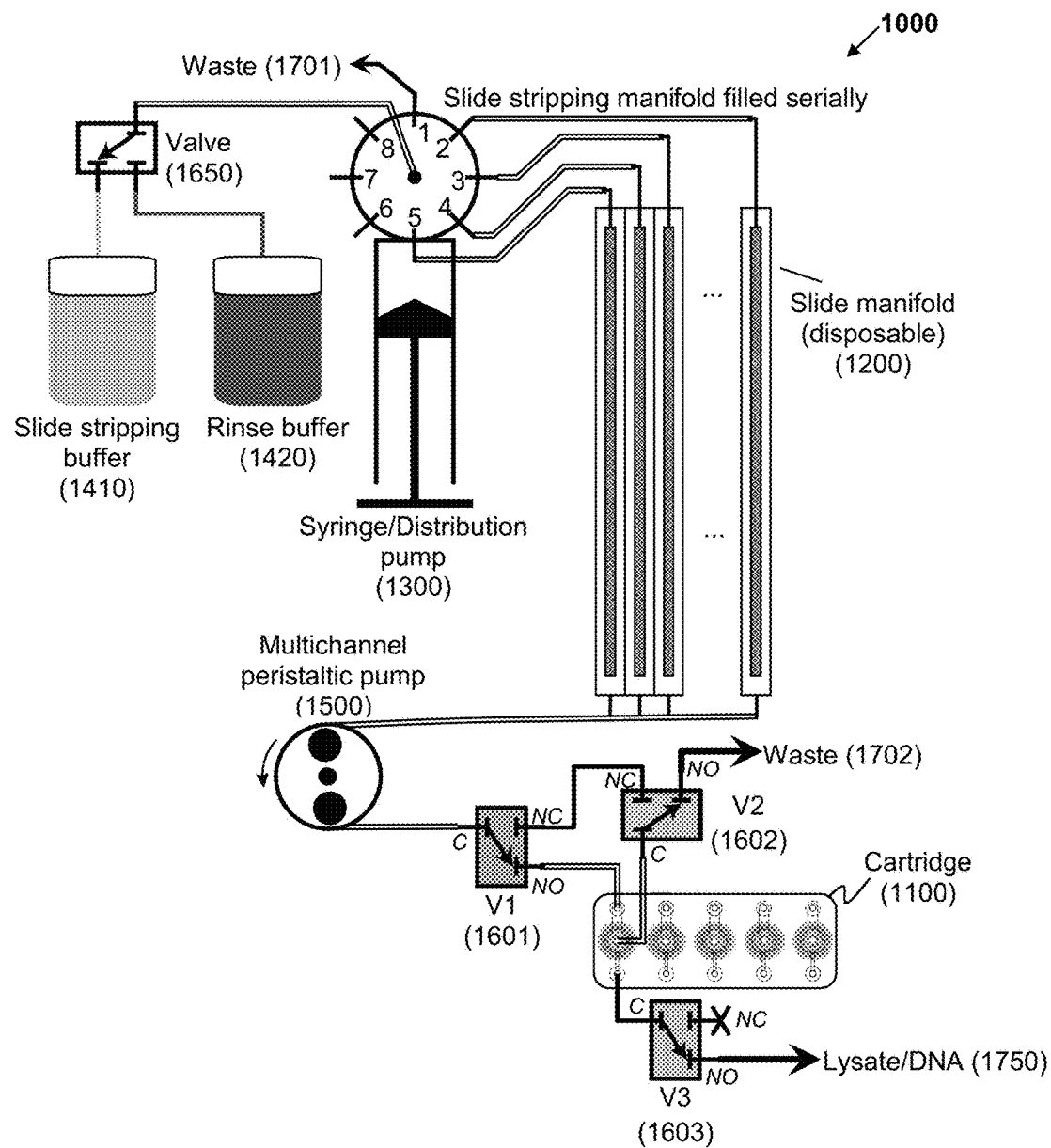
FIG. 7 is a schematic of an exemplary system 1000 having a syringe/distribution pump 1300 for automated use with a slide manifold 1200 and a cartridge 1100.

FIG. 7 is a schematic illustration of a complete slide processing and DNA extraction system 1000 that uses a disposable 5-channel cartridge 1100, a reversibly coupled transducer array, and a pumping system including pumps 1300, 1500. Slide smears can be processed by inserting them serially into disposable slide manifolds 1200 that can be filled with a stripping buffer from a reservoir 1410. The stripping buffer removes the biological sample from the glass surface so that the solution can be pumped into a channel of the cartridge 1100 using a switching syringe/distribution pump injector 1300 and a multi-channel peristaltic pump 1500. Rinse buffer 1420 and stripping buffer 1410 can alternatively be pumped into the channel. Waste 1701 can be collected in a separate channel of the syringe/distribution pump 1300.

Valves can be used throughout the system 1000 to provide fluidic communication between the cartridge, pumping system, pumps, and reservoirs. For instance, a valve 1650 can be placed between the buffer reservoirs 1410, 1420 and the syringe/distribution pump 1300 to alternately transport slide stripping buffer and rinse buffer through the system 1000. In another instance, a valve V1 1601 can be used to transport fluid from the slide washing manifold 1200 to the acoustic lysing cartridge 1100. In some embodiments, the minimal slide washing volume can be about 5 ml for each slide. Other valves can be used to transport fluid from the cartridge (e.g., as described herein, such as for valves V2 1602 and V3 1603).

Fluid can be pumped through the cartridge inlet port to the capture filter membrane, which then collects the target (e.g., DNA, RNA, protein, un-lysed cells, or any target described herein). This process concentrates the target on the filter while eliminating a large portion of extracellular debris and harsh chemicals of the stripping buffer (e.g., by collecting the filtrate through the inlet/outlet connected to the filter of the cartridge). The concentrated target can then be released from the filter with a rinse buffer (e.g., a rinse buffer injected through the inlet of the cartridge), where the lysate flows through the channel in the cartridge to be collected for further analysis. The fluid can be either static or flowing through the lysing portion of the channel during cell lysis.

In one embodiment, the cartridge is a 5-element cartridge 1100. Each of the five lysing/DNA extraction channels can include three valves V1, V2, and V3 (1601, 1602, and 1603), thereby providing a system having 15 valves connected to the inlets and outlets of the cartridge 1100 and a valve 1650 connected to reservoirs 1410, 1420. For simplicity, in FIG. 6, valves are only shown for one element for the cartridge 1100. These valves are used to gate fluid from the stripping manifold 1200 to the cartridge 1100, to process the final lysate or target (e.g., DNA) 1750, or to collect filtrate into the waste reservoir 1702. These valves can be located off-chip or on-chip. Though on-chip valves are often the best solution for miniaturization, off-chip valves may be used to process larger sample volumes.

When the reagents are chemically harsh (e.g., such as for a stripping buffer), the valves preferably have high chemical resistance. Any valve, whether located on- or off-chip, preferably maintains low target binding to the microchannel and to the filter support over the course of this fluid processing step. Of course, biological loss can be greater when locating valves off-cartridge. Therefore, it is preferable to integrate all necessary valves into the cartridge to avoid unnecessary target loss. With acoustic actuation, e.g., the DNA loss can be negligible as compared to the positive control.

Flow rates, channel dimensions, and filter characteristics can be selected to provide the optimal processing speed and accuracy, while avoiding excessive pressure build-up. For instance, to process 5 ml of sample from the manifold in a few minutes, the flow rate can be about 2.5 ml/min. High flow rates can create substantial pressure on the seals, leading to failure especially when the fluidic channels are on the micron scale. The pressure is a direct function of the flow rate, filter area, filter porosity, channel dimensions, tubing inner diameter, and filter hydrophobicity. By using a channel width of 1.6 mm, a flow rate of 2.5 ml/min was attained with a maximum backing pressure of 45 psig. When the filter diameter was increased to 0.58 cm (maximum flow is about 7.79 ml/min) and the channel height increased to 762 μm, the pressure was 25 psig for a flow rate of 2.5 ml/min.

As an example, the system 1000 was used to process MTB simulant *Bacillus* Calmette-Guérin (BCG). First, BCG cells were loaded onto the capture filter using the slide stripping buffer. Then, the loaded cells were released from the filter using either a back-flow or lateral-flow wash. Finally, the released cells were acoustically lysed.

For the cell loading step, BCG was loaded onto the filter using stripping buffer (2.5 ml/min) transported through the cartridge 1100 by using the normally open (NO) position of valve V1 1601 and the NO position of valve V2 1602. Excess stripping buffer exited valve V2 1602 as waste 1702.

For the cell release step, the capture filter was rinsed with a rinse buffer (1×PBS, pH 7.4) using either a back-flow or lateral-flow wash. For the back-flow wash, the rinse buffer was pumped through the filter. To realize this wash step, valve V1 1601 was in the normally closed (NC) position, and rinse buffer was pumped back through valve V2 1602 in the NO position. For the lateral-flow wash, the rinse buffer was pumped through the entire lysing channel. For this step, valve V1 1601 was in the NO position, and valve V2 1602 was in the NC position.

In both the back-flow wash and lateral-flow wash methods, some BCG was lost on the filter support. Some additional loss may have resulted from non-specific binding of BCG-DNA in the microchannel. Buffer and surface modifications can be used to decrease the loss. By using the small porous filter membrane embedded in the cartridge, bacteria from large samples volumes of about 10 ml could be quickly filtered and the DNA extracted within a few minutes at an efficiency of 78%. A skilled artisan would understand that other pumping systems, cartridge modifications, and fluidic configurations could be employed to minimize target loss.

Acoustic Streaming and Focusing

The system can employ any additional technologies to facilitate on-chip sampling processing. For instance, one such technology includes acoustic streaming and focusing, which uses surface acoustic waves that propagate on the surface of a piezoelectric material.

Figure 9:
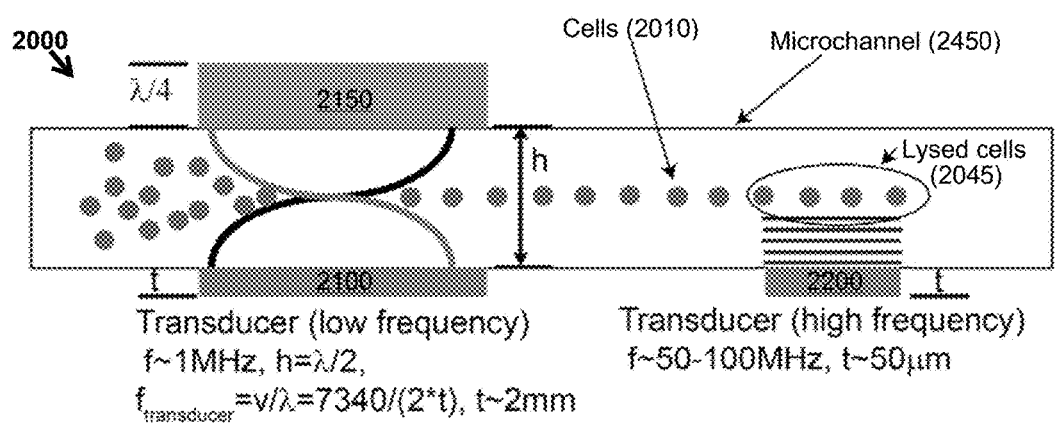
FIG. 9 is a schematic showing an exemplary acoustic lysis system 2000 configured for acoustic focusing of cells 2010.

FIG. 9 is a schematic of an exemplary system 2000 configured for both acoustic focusing and acoustic lysing. As can be seen, a sample including one or more cells 2010 is introduced into the microchannel 2450. A first transducer 2100 (the focusing transducer) focuses the cell samples, and a second transducer 2200 (the lysing transducer) lyses the cells 2045.

The focusing transducer 2100 can have any useful configuration. Generally, focusing requires a half-wavelength in the fluid to create a node where particles or cells concentrate. Also, the top of the microchannel 2450 generally includes an acoustic reflector 2150 to create a standing wave pattern between the reflector 2150 and the focusing transducer 2100.

The focusing and lysing transducers can have any useful geometry and dimension. In particular, the thickness t of the transducer can be adjusted to provide the appropriate wavelength of the acoustic wave within the channel. As can be seen in FIG. 9, the frequency of the transducer f is inversely proportional to t. Thus, higher f is accomplished by employing a lower t, and vice versa. Typically, acoustic focusing will employ lower frequency waves than acoustic lysing, thus the focusing transducer will generally be thicker than the lysing transducer. In one embodiment, the lysing transducer is much thinner to excite waves with a wavelength on order of the size of the cells.

The type of wave is also dictated by the cut and orientation of the piezoelectric substrate. In one non-limiting embodiment, 36°YX lithium niobate is used for both focusing and lysis, provided that the thickness t of the transducers 2100, 2200 is adjusted to achieve the correct wavelength in the medium. In addition, a parallel set of electrodes can be used for focusing and lysis by propagating compression waves into the medium within the microchannel 2450.

Acoustophoresis or acoustic focusing can be beneficial for label-free separation within a sample because the acoustic radiation force exerted on a particle depends on the particle's physical properties, such as size, density, and compressibility. Thus, for example and without limitation, heterogeneous cell samples can be separated based on differing size because cells of different sizes will have different motion responses in the acoustic field.

The transducer can be tuned as appropriate. For instance, the transducer can be tuned to provide the appropriate number of pressure nodes and antinodes in the channel. In one embodiment, in order to provide a single pressure node in the channel, the acoustic frequency is tuned to match about one-half of the wavelength of the channel width. In another embodiment, in order to provide two pressure nodes in the channel, the acoustic frequency is tuned to match the first harmonic resonance mode ($2 \times \lambda/2$), thereby providing two focusing streams. In a similar manner, a plurality of pressure nodes can be established by appropriate acoustic tuning.

Further structures and components for acoustic streaming and focusing (e.g., piezoelectric materials, electrodes, acoustic waveguides, acoustic reflectors, etc.) are described in U.S. Pat. No. 7,942,568; Branch D W et al., "Intelligent front-end sample preparation tool using acoustic streaming," Sandia Report No. SAND2009-6193, September 2009 (70 pages); Yeo L Y et al., "Ultrafast microfluidics using surface acoustic wave," *Biomicrofluidics* 2009 Jan. 2; 3(1):12002 (23 pages); Yeo L Y et al., "Surface acoustic wave microfluidics," *Annu. Rev. Fluid Mech.* 2014; 46:379-406; Jung B et al., "Acoustic particle filter with adjustable effective pore size for automated sample preparation," *Anal. Chem.* 2008 Nov. 15; 80(22):8447-52; Ai Y et al., "Separation of *Escherichia coli* bacteria from peripheral blood mononuclear cells using standing surface acoustic waves," *Anal. Chem.* 2013 Oct. 1; 85(19):9126-34; Shi J et al., "Continuous particle separation in a microfluidic channel via standing surface acoustic waves (SSAW)," *Lab Chip,* 2009 Dec. 7; 9(23):3354-9; Adams J D et al., "Integrated acoustic and magnetic separation in microfluidic channels," *Appl. Phys. Lett.* 2009 Dec. 21; 95(25):254103 (3 pages); and Yang A H J et al., "Acoustophoretic sorting of viable mammalian cells in a microfluidic device," *Anal. Chem.* 2012 Dec. 18; 84(24):10756-62, each of which is incorporated herein by reference in its entirety.

Optionally, acoustic streaming can be combined with other functionalities. Exemplary functionalities include acoustic focusing (e.g., employing a piezoelectric transducer) combined with dielectrophoretic focusing (e.g., employing an electrode array, such as any described herein), as described in U.S. Pat. No. 8,425,749; and Ravula S K et al., "A microfluidic system combining acoustic and dielectrophoretic particle preconcentration and focusing," *Sens. Actuat. B* 2008; 130:645-52; and tunable separation employing a plurality of independently controlled, serially connected stages, each characterized by a channel width w, and piezo actuation amplitude V and frequency f (Adams J D et al., "Tunable acoustophoretic band-pass particle sorter," *Appl. Phys. Lett.* 2010 Aug. 9; 97(6):064103 (3 pages)), where each reference is incorporated herein by reference in its entirety.

Other Components

The present system can include one or more additional components. Such components can be provided on-chip or off-chip. In addition, such components can be integrated into the same cartridge for acoustic lysis or, alternatively, incorporated in a separate cartridge in fluidic communication with the cartridge for acoustic lysis.

The system can include one or more interdigital transducers (IDTs), including chirped IDTs; function generators; amplifiers; pumps; valves; fluidic connectors; surface acoustic wave sensors, such as those described in U.S. Pat. Nos. 7,878,063, 8,436,509, 8,669,688, and U.S. Pub. No. 2011-0053139, each of which is incorporated herein by reference in its entirety; resonators, such as a Fabry-Perot cavity, e.g., as described in U.S. Pat. No. 8,525,619, which is incorporated herein by reference in its entirety; electrodes, such as those having one or more interdigitated electrodes of opposing comb-shaped electrodes, microelectrodes (e.g., having a critical dimension on the range of 1 to 1000 μm, such as a radium, width, or length from about 1 to 1000 μm), or nanoelectrodes (e.g., having a critical dimension on the range of 1 to 100 nm, such as a radium, width, or length from about 1 to 100 nm), which are optionally passivated with Nafion® (a sulfonated tetrafluoroethylene based fluoropolymer-copolymer and/or provided in an array; and/or an RF drive circuit for the system, such as including a tunable RF source, an RF power amplifier, a controller, a power splitter, (see, e.g., Branch D W et al., Sandia Report No. SAND2009-6193, September 2009 (70 pages)).

In particular, the system can include one or more capture agents that bind to a target. Exemplary capture agents include one or more filters, beads (e.g., magnetic beads, such as ChargeSwitch® beads, as described in Branch D W et al., Sandia Report No. SAND2009-6193, September 2009 (70 pages)), matrices (e.g., a sol-gel matrix including one or more beads, such as that described in Branch D W et al., Sandia Report No. SAND2009-6193, September 2009 (70 pages)), filter plugs, and/or extraction matrices (e.g., including a gel, such as a sol-gel, agarose, etc.).

To transport one or more fluids through the cartridge, the system can include a pumping system, which can be integrated with the cartridge and/or platform or, alternatively, be provided as an external component. Exemplary pumping systems include a pneumatic pressure source; a vacuum source; a pressurized (or evacuated) canister, chip, or other container; a compressor; a membrane pump; an electrophoretic or electroosmotic pump; and/or a vacuum pump, each of which may be located inside the cartridge, inside the platform, or outside of the system. When an external pumping system is used, the cartridge can include one or more inlets, outlets, ports, vents, channels, etc. for fluidic communication with the pumping system.

For some analysis or detection modalities, controlled heating may be beneficial. For instance, PCR amplification can employ thermal cycling for polymerase and ligase chain reactions. In another instance, heating can facilitate mixing, dissolution, denaturation, elution, etc. Accordingly, the system can include one or more resistive heaters (e.g., employing thin-film metal, carbon, or polysilicon at selected regions).

One or more detection components can be used for detection by electrochemical, colorimetric, fluorescent, western blot, immunohistochemistry, immunoassay (e.g., lateral flow assay), immunochromatography, radio immunoassay, optical immunoassay, enzyme immunoassay, chemiluminescence, and/or electrochemiluminescence methods in any useful format. Exemplary detection components include a transducer, such as an optical sensor (e.g., including measuring one or more of fluorescence spectroscopy, interferometry, reflectance, chemiluminescence, light scattering, surface plasmon resonance, or refractive index, such as by employing a light emitting diode (LED) and a photodetector), a piezoelectric sensor (e.g., including one or more quartz crystals, such as a Love wave sensor, a surface acoustic wave sensor, a bulk acoustic wave sensor, or a quartz crystal microbalance), an electrochemical sensor (e.g., one or more of carbon nanotubes, electrodes, field-effect transistors, etc.), an ion selective electrode, an ion sensitive field effect transistor (e.g., a n-p-n type sensor), a light addressable potentiometric sensor, an amperometric sensor (e.g., having a two-electrode configuration (including reference and working electrodes) or a three-electrode configuration (including reference, working, and auxiliary electrodes)), an impedimetric sensor, a disk electrode, a spherical electrode, a plate electrode, a hemispherical electrode, a planar electrode, a three-dimensional electrode, a porous electrode, a post electrode, a microelectrode (e.g., having a critical dimension on the range of 1 to 1000 μm, such as a radium, width, or length from about 1 to 1000 μm), or a nanoelectrode (e.g., having a critical dimension on the range of 1 to 100 nm, such as a radium, width, or length from about 1 to 100 nm), as well as arrays thereof; capillary beds, such as a lateral flow assay for immunoassays and sandwich assays; fiber optics, such as for excitation and collection for fluorescence detection; and/or integrated wave-guides, circular or elliptical microlenses, and/or photodiodes, as well as arrays thereof.

Additional components can be included, such as one or more of the following: a power source (e.g., such as a battery that provides power to the pumps, valves, or acoustic transducers); a separation/extraction component (e.g., filters, posts, membranes, weirs (optionally including beads), matrices, or high voltage electrodes for performing on-chip capillary electrophoresis separations); a heating component (e.g., electrodes, filaments, or resistive heaters, such as for PCR amplification); pumps (e.g., active or passive pumps, such as a low flow rate peristaltic pump or application of negative pressure, such as by actuating a valve); a membrane (e.g., placed within a channel and/or a chamber); a multi-functional sensor (e.g., to measure temperature, strain, and electrophysiological signals, such as by using amplified sensor electrodes that incorporate silicon metal oxide semiconductor field effect transistors (MOSFETs), a feedback resistor, and a sensor electrode in any useful design, such as a filamentary serpentine design); a microscale light-emitting diode (LEDs, such as for optical characterization of the test sample); an active/passive circuit element (e.g., such as transistors, diodes, and resistors); an actuator; a wireless power coil; a device for radio frequency (RF) communications (e.g., such as high-frequency inductors, capacitors, oscillators, and antennae); an RF circuit (e.g., any provided herein); a resistance-based temperature sensor; a photodetector; a photovoltaic cell; a diode; a data-processing circuit powered by the power source and electrically connected to the transducer (e.g., by way of a counter electrode, a reference electrode, and at least one said working electrode); and/or one or more components for autonomous remote monitoring of a sample, such as an analog-to-digital converter, a radiofrequency module, and/or a telemetry unit (e.g., configured to receive processed data from a data-processing circuit electrically connected to the platform and to transmit the data wirelessly).

In particular embodiments, the system and device of the invention encompasses components to facilitate high throughput processing. For instance, the system or device includes one or more arrays of parallel fluidic channels to allow for parallel processing. In further embodiments, the fluidic channels are nanofluidic or microfluidic channels (e.g., to minimize sample volume and consumption). Additional miniaturized systems and modifications are provided in U.S. Pat. Nos. 6,168,948, 6,887,693, and 7,785,868; Nan L et al., "Emerging microfluidic devices for cell lysis: a review," *Lab Chip*, 2014 Feb. 17; 14(6):1060-73; Reboud J et al., "Shaping acoustic fields as a toolset for microfluidic manipulations in diagnostic technologies," *Proc. Nat'l Acad. Sci. USA*, 2012 Sep. 18; 109(38):15162-7; Marentis T C et al., "Microfluidic sonicator for real-time disruption of eukaryotic cells and bacterial spores for DNA analysis," *Ultrasound Med. Biol.* 2005 September; 31(9):1265-77; and Belgrader P et al., "A minisonicator to rapidly disrupt bacterial spores for DNA analysis," *Anal. Chem.* 1999 Oct. 1; 71(19):4232-6, each of which is incorporated herein by reference in its entirety.

Methods of Making Cartridges, Platforms, and Systems

The cartridges, platforms, and systems of the invention can be formed by any useful process. Exemplary processes include microfabrication techniques, such as those regularly used in the semiconductor and microelectronics industries, are particularly suited to these materials and methods. These techniques include, e.g., electrodeposition, low-pressure vapor deposition, glass bonding, photolithography, wet chemical etching, reactive ion etching (RIE), laser drilling, and the like. Where these methods are used, it will generally be desirable to fabricate the planar members of the cartridge from materials similar to those used in the semiconductor industry, i.e., polymers, silica glass, silicon, gallium arsenide, polyimides, metal films, and the like. In additional embodiments, the cartridge may comprise a combination of materials and manufacturing techniques described above. In some cases, the cartridge may include some parts of injection molded plastics, and the like, while other portions of the body may comprise etched glass or silicon members, and the like.

The components of the system can be made for optimal interaction. For instance, the cartridge may be fabricated in such a way that specific regions or regions interact with the platform, the platen, and/or an external instrument. Many plastics commonly used for such cartridges (e.g. polypropylene and polycarbonate) are optically transparent. In general, insulating materials allow electromagnetic radiation to pass over a wide frequency range. Such radiation may be of any frequency consistent with the intended application. For example, radio waves may be used as an alternative means of communicating with the cartridge. Radio waves may also be used to supply small amounts of power to any internal circuitry within the cartridge. Microwave frequencies may be used to induce heating of the fluid sample. Infrared signals may be used for heating, or for data exchange via an IR link, similar to those used in personal computers.

The present cartridges, platforms, and systems of the invention can be formed from any useful material. Exemplary materials include a polymer (e.g., any described herein), such as polymethyl methacrylate (PMMA), polyethylene terephthalate (PET, e.g., biaxially-oriented PET or bo-PET), an acrylic polymer, poly(dimethylsiloxane) (PDMS), or polycarbonate (PC); silicon; glass; a thermal exchange material, such as any described herein; an adhesive, such as any described herein; as well as combinations thereof (e.g., combinations of such materials provided in separate layers or within the same layer).

Any surface of the cartridges, platforms, and systems can be modified. For instance, the surfaces of the fluidic regions that contact the fluid sample and reagents may be made hydrophobic or hydrophilic depending upon the particular application. Where reagents involved in a particular analysis are incompatible with the materials used to manufacture the cartridge, e.g., silicon, glass or polymeric parts, a variety of coatings may be applied to the surfaces of these parts that contact the reagents. For example, components that have silicon elements may be coated with a silicon nitride layer or a metallic layer of, e.g., gold or nickel, sputtered or plated on the surface to avoid adverse reactions with these reagents.

Methods of Use

The present invention includes methods that use the cartridges, platforms, and systems described herein. Exemplary uses include methods of preparing a sample (e.g., a biological sample), methods of determining the presence of a target (e.g., any target described herein), and methods of lysing a cell.

In one instance, the method to lyse a cell (e.g., biological, animal, plant, and/or pathogen cells, such as viruses, bacteria, T-cells, mammalian cells, etc.) includes pumping a sample through a channel of a cartridge or system described herein, thereby capturing the biological cells on a filter; releasing the capturing biological cells from the filter using a rinse buffer; and lysing the biological cells in the rinse buffer in the lysing portion of the cartridge or system, thereby releasing the cellular content (e.g., genomic material, such as DNA, RNA, or un-denatured proteins) from the biological cells. In some embodiments, the rinse buffer is static or flowing (e.g., in the lysing portion during lysing). In some embodiment, the method include, prior to the pumping step, stripping a sample including biological cells from a slide smear using a stripping buffer.

The methods herein can be useful for diagnostics (e.g., POC diagnostics). In particular, the system can be adapted to perform POC detection and monitoring of infectious diseases at resource-limited settings. POC diagnostics should be able to analyze small volumes of bodily fluids, e.g., blood, saliva, sputum, and urine, and the cartridges of the invention easily accommodate such small volumes with minimal sample loss and multiplexed fluid handling.

Furthermore, the methods and technologies can be applicable for nucleic acid and protein assays that are sensitive to background chemicals, such as real-time polymerase chain reaction (RT-PCR). Such assays can be beneficial to discriminate among infectious and potentially lethal bacteria and fungi, where extracted DNA and/or RNA of the sample can be analyzed by any useful methodology (e.g., by RT-PCR). To extract nucleic acid (e.g., RNA and/or DNA), the cartridge can use several integrated approaches, such as, e.g., magnetic beads, electrostatic capture, or filtration methods (see, e.g., FIG. 6B). The systems and methods herein are suitable to perform sample preparation steps, which can be combined with any useful diagnostic methods (e.g., immunoassays, fluorescence, absorbance, chemiluminescence, and/or SPR).

Because the present system uses sound waves but not harsh chemical or mechanical methods to lyse cells, relatively unharmed and unmodified DNA, RNA and proteins can be obtained. As further sample purification or separation steps are not required, this technology allows molecular diagnosis to be done quickly, portably, and without other cumbersome reagents both in traditional medical clinics or in those in underprivileged or remote settings. Accordingly, the present invention includes systems and devices for use with DNA and RNA analysis, such as by including one or more reagents or probes specific for the target DNA and/or RNA.

In particular, the system can be used to detect MTB and multi-drug resistant forms on a rapid basis and even in a remote setting. Generally, drug susceptibility testing determines the ability of the four primary antibiotics to inhibit in vitro growth of *M. tuberculosis* complex (MTBC). Such testing requires culturing of MTB and then inoculating MTB-positive cultures onto antibiotic-containing media or into antibiotic-containing BACTEC™ MGIT™ bottles. As MTB has a slow growth rate, traditional culture-based drug susceptibility tests can require several weeks or months to complete (Palomino J C et al., "Rapid culture-based methods for drug-resistance detection in *Mycobacterium tuberculosis*," J. Microbiol. Methods 2008 October; 75(2):161-6). The present system allows for an accurate and timely accounting of drug resistance rates, making it possible to estimate risk for each type of drug resistance by geographic region and patient profile, and to develop treatment algorithms accordingly. Such a system should be adapted to release MTB DNA for PCR identification, sequencing, and susceptibility profiling through mutation analysis.

The cartridge, system, and methods can allow for other specified chemical or biological interactions. The operations enabled by specific chemical interactions include specimen volume dilution; pH adjustment; biochemical solubilization; molecular aggregation; cellular or viral lysis; agglutination of target cells or capture-particles; filtration; flocculation; neutralization; specific analyte extraction and purification; contaminant extraction and separation; precipitation of specific molecules; binding of analyte to reporter moieties; and dried reagent reconstitution.

Kits

The present system can further be provided in a kit. The kit can include one or more of the following: a collection swab for collecting the test sample, a cartridge, a source for energizing the transducer (e.g., a portable power source, such as a battery), an external heater for incubating the test sample within the cartridge, a platform of the invention, a platen, a pumping system, a pressure source (e.g., a compressed air container to pump one or more fluids through the channel), and/or a telemetry unit (e.g., any described herein).

Targets and Samples

The present system and cartridge can be used to detect any useful targets. Exemplary targets include a bacterium, such as Mycobacteriaceae (e.g., M. tuberculosis, M. bovis, or M. leprae), Bacillus (e.g., B. anthracis), Enterobacteriaceae (e.g., Salmonella, Escherichia coli, Yersinia pestis, Klebsiella, and Shigella), Yersinia (e.g., Y. pestis or Y. enterocolitica), Staphylococcus (e.g., S. aureus), Streptococcus, Gonorrheae, Enterococcus (e.g., E. faecalis), Listeria (e.g., L. monocytogenes), Brucella (e.g., B. abortus, B. melitensis, or B. suis), Vibrio (e.g., V. cholerae), Corynebacterium diphtheria, Pseudomonas (e.g., P. pseudomallei or P. aeruginosa), Burkholderia (e.g., B. mallei or B. pseudomallei), Shigella (e.g., S. dysenteriae), Rickettsia (e.g., R. rickettsii, R. prowazekii, or R. typhi), Francisella tularensis, Chlamydia psittaci, Coxiella burnetii, Mycoplasma (e.g., M. mycoides), etc.; allergens, such as peanut dust, mycotoxins, mold spores, or bacterial spores such as Clostridium botulinum and C. perfringens; toxins, such as ricin, mycotoxin, tetrodotoxin, anthrax toxin, botulinum toxin, staphylococcal entertoxin B, or saxitoxin; a virus, such as Adenoviridae (e.g., adenovirus), Arenaviridae (e.g., Machupo virus), Bunyaviridae (e.g., Hantavirus or Rift Valley fever virus), Coronaviridae, Orthomyxoviridae (e.g., influenza viruses), Filoviridae (e.g., Ebola virus and Marburg virus), Flaviviridae (e.g., Japanese encephalitis virus and Yellow fever virus), Hepadnaviridae (e.g., hepatitis B virus), Herpesviridae (e.g., herpes simplex viruses), Papovaviridae (e.g., papilloma viruses), Paramyxoviridae (e.g., respiratory syncytial virus, measles virus, mumps virus, or parainfluenza virus), Parvoviridae, Picornaviridae (e.g., polioviruses), Poxviridae (e.g., variola viruses), Reoviridae (e.g., rotaviruses), Retroviridae (e.g., human T cell lymphotropic viruses (HTLV) and human immunodeficiency viruses (HIV)), Rhabdoviridae (e.g., rabies virus), and Togaviridae (e.g., encephalitis viruses, yellow fever virus, and rubella virus)); a protozoon, such as Cryptosporidium parvum, Encephalitozoa, Plasmodium, Toxoplasma gondii, Acanthamoeba, Entamoeba histolytica, Giardia lamblia, Trichomonas vaginalis, Leishmania, or Trypanosoma (e.g., T. brucei and T. Cruzi); a helminth, such as cestodes (tapeworms), trematodes (flukes), or nematodes (roundworms, e.g., Ascaris lumbricoides, Trichuris trichiura, Necator americanus, or Ancylostoma duodenale); a parasite (e.g., any protozoa or helminths described herein); a fungus, such as Aspergilli, Candidae, Coccidioides immitis, and Cryptococci; an environmental contaminant; a water additive; an agricultural marker; a nucleic acid (e.g., oligonucleotides, polynucleotides, nucleotides, nucleosides, molecules of DNA, or molecules of RNA, including a chromosome, a plasmid, a viral genome, a primer, or a gene); a protein (e.g., a glycoprotein, a metalloprotein, an enzyme, a prion, or an immunoglobulin); a metabolite; a sugar; a lipid; a lipopolysaccharide; a salt; or an ion.

Targets also include food-borne pathogens, such as Salmonella (e.g., Salmonella Typhimurium), pathogenic E. coli (e.g., O157:H7), Bacillus (e.g., B. cereus), Clostridium botulinum, Listeria monocytogenes, Yersinia (e.g., Y. enterocolitica), Norovirus (e.g., Norwalk virus), Shigella, Staphylococcus aureus, Toxoplasma gondii, Vibrio (e.g., V. vulnificus, V. cholera, V. parahaemolyticus), Campylobacter jejuni, and Clostridium perfringens; and weaponized pathogens, such as Bacillus anthracis, Yersinia pestis, Francisella tularensis, Brucella (e.g., B. suis), Burkholderia mallei, Burkholderia pseudomallei, Shigella, Clostridium botulinum, Variola (e.g., V. major), Filoviridae (e.g., Ebola virus and Marburg virus), Arenaviridae (e.g., Lassa virus and Machupo virus), Clostridium perfringens, any food-borne pathogen (e.g., Salmonella species, Escherichia coli O157:H7, or Shigella), Chlamydia psittaci, Coxiella burnetii, Staphylococcal aureus, Rickettsia (e.g., R. prowazekii or R. rickettsii), Alphavirus (e.g., Venezuelan equine encephalitis virus, eastern equine encephalitis virus, or western equine encephalitis virus), Vibrio cholerae, Cryptosporidium parvum, Henipavirus (e.g., Nipah virus), Bunyaviridae (e.g., Hantavirus or Rift Valley fever virus), Flaviviridae (e.g., Japanese encephalitis virus and Yellow fever virus), and Coccidioides spp., as well as drug-resistant forms of any of these (e.g., active multidrug-resistant Mycobacterium tuberculosis).

The test sample can include any useful sample, such as a microorganism, a virus, a bacterium, a fungus, a parasite, a helminth, a protozoon, a cell, tissue, a fluid, a swab, a biological sample (e.g., blood, serum, plasma, saliva, sputum, urine, etc.), a protein, a nucleic acid (e.g., genomic DNA, RNA, miRNA, etc.), an environmental sample, etc.

Other targets include pathogenicity islands from nucleic acid samples, which can be assessed to determine the pathogenicity of the target bacteria (Gal-Mor O et al., "Pathogenicity islands: a molecular toolbox for bacterial virulence," Cell. Microbiol. 2006 November; 8(11):1707-19).

Reagents

The present cartridge can include any number of useful reagents on-chip or off-chip. One or more fluids can be used to transport the sample (e.g., using a buffer, such as any described herein), to elute the target from a solid support (e.g., using an elution fluid), to remove a biological component from a surface (e.g., using a stripping buffer to remove proteins or cells from a surface), and/or to transport one or more capture agents or probes. Additional reagents are described below.

Exemplary reagents includes one or more buffers, e.g., saline, phosphate buffers, borate buffers, TRIS buffers, HEPES buffers, acids, bases, detergent solutions, chaotropic solutions, nucleic acid amplification buffers, and nucleic acid hybridization buffers, where each can optionally include a salt (e.g., NaCl, $MgCl_2$, or $CaCl_2$), a preservative (e.g., EDTA), a detergent (e.g., a polysorbate), a cryoprotectant (e.g., glycerol), and/or a stabilizer (e.g., dimethyl sulfoxide); elution fluids, e.g., molecular grade pure water, a buffer (e.g., any described herein), including but not limited to a solution of TRIS (optionally including a salt, such as NaCl; a preservative, such as ethylenediamine tetraacetic acid (EDTA); or a detergent, such as TWEEN, a polysorbate), TRIS/acetate/EDTA (e.g., 4 mM Tris-acetate (pH 7.8), 0.1 mM EDTA, and 50 mM NaCl), TRIS/borate (optionally including a preservative, such as EDTA), potassium phosphate/DMSO/glycerol, phosphate buffers, HEPES buffers, nucleic acid amplification buffers, and nucleic acid hybridization buffers; an antibiotic, e.g., isoniazid, rifampin, ethambutol, or pyrazinamide; an enzyme, such as a polymerase, a ligase, a transcriptase, a phosphatase, a peroxidase, or a redox enzyme (e.g., horseradish peroxidase or glucose oxidase); a detection agent, e.g., a dye, such as an electroactive or electrocatalytic detection agent (e.g., a mediator chemical (an 'electron shuttle')), a fluorescent dye, a luminescent dye, a chemiluminescent dye, a colorimetric dye, a radioactive agent, or a J-aggregate dye, such as those described in Whitten D G et al., "Cooperative self-assembly of cyanines on carboxymethylamylose and other anionic scaffolds as tools for fluorescence-based biochemical sensing," *Pure Appl. Chem.* 2006; 78(12):2313-23; a particle, such as a microparticle, a nanoparticle, a latex bead, a colloidal particle, a magnetic particle, a fluorescent particle, etc.; a label, such as an electroactive label, a redox active chemical (e.g., ferricyanide, ferrocene, ruthenuim bipyridine, etc.), an electrocatalytic label, a fluorescent label, a colorimetric label, a quantum dot, a nanoparticle, a microparticle, a barcode, a radio label (e.g., an RF label or barcode), avidin, biotin, a tag, a dye, a marker, an enzyme that can optionally include one or more linking agents and/or one or more dyes; an amplifying agent, such as a PCR agent, e.g., a polymerase, a ligase, a transcriptase, one or more deoxyribonucleotide triphosphates or modified nucleotides (e.g., inosine), a divalent metal (e.g., $MgCl_2$), a template DNA, and/or a primer (e.g., for binding to a selective region of the target nucleic acid, such those encoding for a pathogenicity island, a mutation region indicative of MDR, or a genomic region specific for *M. tuberculosis*); a capture agent, such as a nucleic acid that binds to a particular region in the target genomic sequence, a protein that binds to or detects one or more markers (e.g., an antibody or an enzyme), an antibody, a globulin protein (e.g., bovine serum albumin), a nanoparticle, a microparticle, a sandwich assay reagent, a catalyst (e.g., that reacts with one or more markers), and/or an enzyme (e.g., that reacts with one or more markers, such as any described herein); a cell medium (e.g., selective media or other additives to select for or give advantage to a particular biological target during microculture, including agar; nutrient media; minimal media; differential media; nutrient broth; or brain-heart infusion broth, where any of these can optionally include one or more antibiotics to select for or against particular targets, one or more nutrients (e.g., a carbon source, such as glucose), one or more enzymes, one or more host cells, and/or one or more salts; a detergent, such as sodium dodecyl sulfate (SDS); a surfactant, e.g., Tween 20, Triton X-100, glycerin, polyvinylalcohol (PVA), polyvinylpyrrolidone (PVP), or polyethylene glycol (PEG); an alcohol, e.g., from about 1% v/v to about 10% v/v methanol, ethanol, or isopropanol; a preservative (e.g., sucrose or trehalose); a blocking agent (e.g., gelatin, casein, bovine serum albumin, IgG, PVP, or PVA); a bead (e.g., a glass bead, silica bead, etc.); a sterilization agent (e.g., a bleach, such as sodium hypochlorite or calcium hypochlorite; an oxidizer, such as chlorine dioxide, sodium dichloroisocyanurate, a peroxide, ethylene oxide, ozone gas, peracetic acid, hypochlorous acid, etc.; a surfactant, such as a cationic, anionic, nonionic, or zwitterionic surfactants, as well as combinations thereof; a catalyst; a phage, e.g., a bacteriophage; a disinfectant, such as glutaraldehyde, stabilized hydrogen peroxide, peracetic acid, or formaldehyde; a biocide; an antiseptic; a detergent; a deodorant; and combinations thereof, where the sterilization agent can be in gas, liquid, semi-solid, or solid form, such as a powder, pellet, granule, gel, lyophilized, or freeze-dried forms), etc., as well as combinations thereof.

Any of the reagents may be provided as a dried form. For instance, dried reagents can be employed as precursor materials for reconstitution and solution-phase interaction or as solid-phase reagents, including pH indicators; redox indicators; enzymes, such as horseradish peroxidase, alkaline phosphatase, reverse transcriptase, DNA polymerase, and restriction enzymes; enzyme substrates; enzyme-antibody or enzyme-antigen conjugates; DNA primers and probes; buffer salts; and detergents. Furthermore, solid-phase reagent coatings such as serum albumin, streptavidin, and a variety of cross-linkable proteins such as polysaccharides may be employed in the channels or chambers of the cartridge.

One or more reagents can be combined together. For instance, a detection agent can be combined with an antibody or with a particle (e.g., a nanoparticle). Exemplary combinations include one or more nanoparticles, enzymes, or chemicals that are directly or indirectly attached (e.g., by a linking agent or a conjugate pair (e.g., biotin-avidin)) to antibodies or other capture reagents.

EXAMPLES

Example 1

Acoustic Lysis System Having a Thermal Exchange Layer

When performing biological assays, heating must be controlled in order to preserve the biologically relevant conformation of DNA and proteins. For instance, uncontrolled heating can result in loss of secondary, tertiary, and/or quaternary structure. Here, we describe an acoustic lysis system adapted to minimize sample heating. This system includes a thermal exchange layer disposed between the sample and the transducer array, as well as a heatsink on the bottom side of the transducer array to further conduct heat away from the sample.

FIG. 2 provides an exemplary lysis system 100 including a cartridge 140 and a transducer 120. As described herein, the system of the invention can include an array of a plurality of elements. For instance, the system can include a cartridge having a fluidic array that includes a plurality of channels, as well as a platform having a transducer array that includes a plurality of acoustic transducers.

The cartridge 140 includes a microchannel 145 formed therethrough. For the laminate acrylic cartridge, microchannel features were cut in thin cell cast acrylic sheets (Techplast Coated Products, Inc., Baldwin, N.Y.) using a $CO_2$ laser. The layers were bonded together using acrylic-based solvents (Weld-On® #4 (a solvent cement including stabilized methyl methacrylate monomer, trichloroethylene, and methylene chloride), from IPS Corp., Compton, Calif.; and Acrifix® 1S 0117 (a solvent acrylic cement including ethyl formate, nitroethane, butan-1-ol, ethyl acetate, and 2-phenoxyethanol), from Evonik Cyro LLC, Parsippany, N.J.) under pressure to create water tight seals between the layers. The thickness of each layer ranged between 8 and 20 mils.

As shown in FIG. 2, the system includes a heatsink 110 and a thermal exchange layer 130 including aluminum nitride (AlN), which supports the transducer. One or more conductive adhesive layers 161, 162 can be used to pattern, adhere, or encapsulate the transducer(s), support layer(s), thermal exchange layer(s), and/or heatsink layer(s). The addition of a heatsink on the backside of the BAW array dramatically limited sample heating. The AlN thermal exchange layer improved power handling capability due to its high thermal conductivity of 150 W/m·K and thermal diffusivity of $3.14 \times 10^{-6}$ m$^2$/sec, reducing internal heat accumulation. A key factor is this lysing system nearly eliminates heating within the microchannels.

The thermal data strongly suggests that proteins retain their native conformation post lysis. Temperature rise is only 4° C. above ambient after 30 seconds of treatment. To avoid denaturing proteins, heating liquid inside the microchannel was kept to a minimum due to the large heat conduction property of the aluminum nitride layer.

TABLE I

Form factor of multichannel BAW lysing system

Single BAW Transducer (3 mm diameter)

| Volume (mm$^3$) | Power Consumption (W) | Emitted Acoustic Power (W) | Power Density of a Single BAW Transducer (W/m$^3$) | Volume (m$^3$) | Support Hardware and Electronics excluding PC Power Consumption (W) |
|---|---|---|---|---|---|
| 52 | 3.8 | 0.16 | $3.1 \cdot 10^6$ | 0.03 | 70.4 |

The form factor and power consumption of the exemplary transducer and supporting hardware are shown in Table I. The return loss (S11) of this exemplary cartridge/transducer combination at operating at 68 MHz is shown is FIG. 4. Return loss is a measure of how well power is coupled to the device, where −3 dB is the break-even point where 50% power is reflected. The return loss shows excellent power transfer to the device (about 98% of the power is transferred to the device, which eliminates the need for matching circuits), which has a bandwidth of 3.6 MHz. Larger bandwidths are possible with this device, but the return loss could degrade power transfer.

Example 2

Acoustic Lysis System for DNA Extraction and Detection

The acoustic lysis system of the invention can include any number of components to facilitate detection. For instance, DNA detection from a whole cell sample requires sample injection, cell lysis, as well as DNA extraction. Described herein is a system including a manifold to facilitate sample injection, a thermal exchange layer to minimize sample heating during lysis, and a filter layer to capture the target DNA. Also described are valve configurations that minimize DNA loss.

The cartridge for cell lysis and DNA extraction can be a multilayered device composed of various composite layers. FIG. 3A-3B provides a composite cartridge composed of six layers: a plastic acoustic coupling layer 243, two microchannel fluid layers 241, 242, two filter layers 260, 261, and an o-ring layer having fluid ports 270. The device can include one or more capping layers above the o-ring layer. The layers are bonded together to form a single assembly by solvent welding. The bottom section 202 serves as a breakaway portion for layer alignment.

For parallel lysis applications, only a single transducer is used to allow more lysing channels per cartridge. As can be seen, the system in FIG. 3B provides five independent lysing channels/element 205 per die 201. In FIG. 3C-3D, each element 205 includes a lysis channel 245, one or more fluidic ports 271-273, one or more inlets/outlets 281-283, one or more fluidic connectors (e.g., an o-ring 290), a filter 260, and a filter support structure 263 including one or more channels. The cartridge 200 can include one or more fluidic connecting regions 291-293 having one or more connectors (e.g., o-rings, valves, or any described herein). The interface 244 between the channel 245 and the single bulk acoustic wave transducer 220 can include a thermal exchange layer.

Figure 3E:
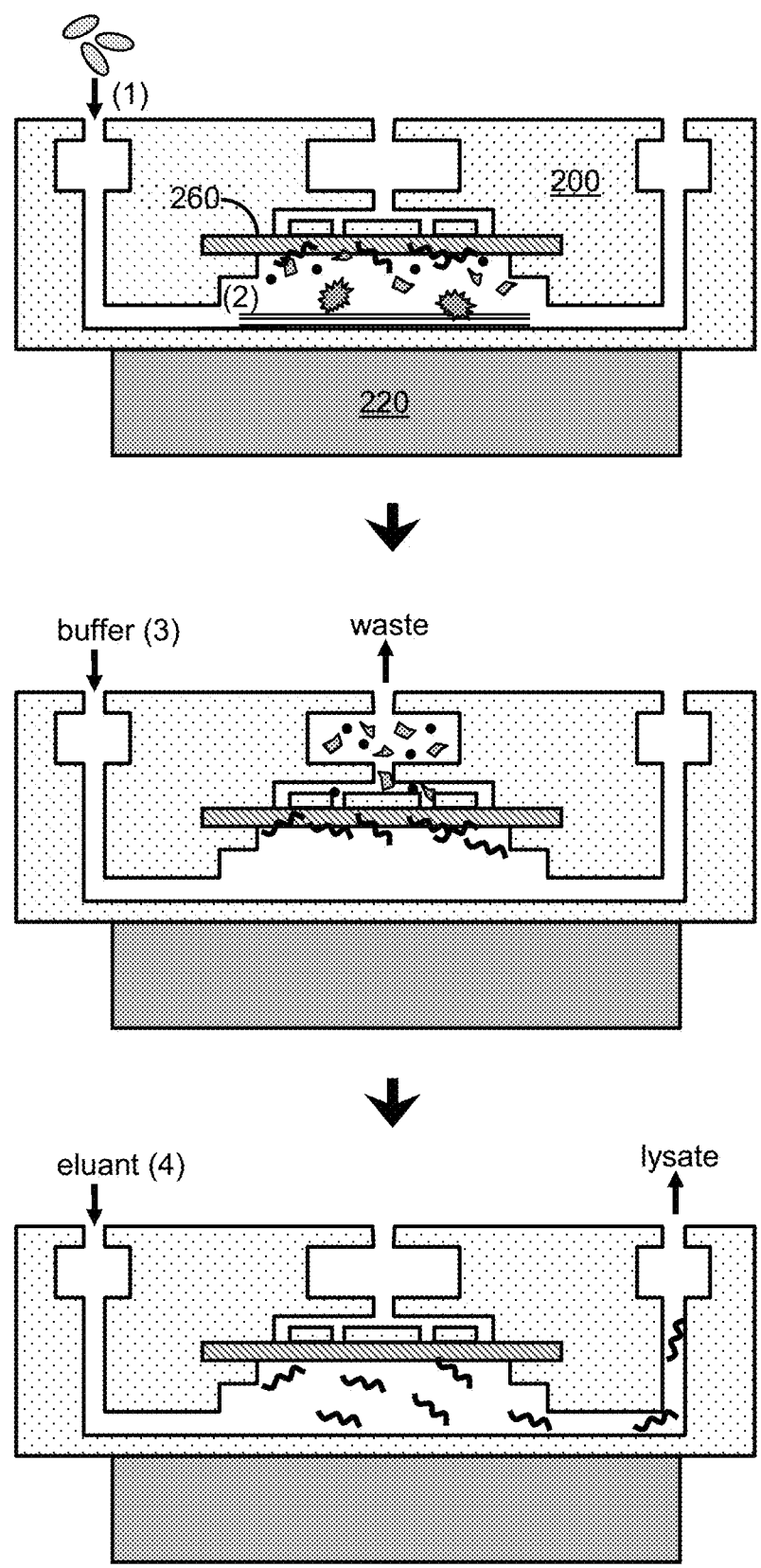

In use (as shown in FIG. 3E), raw samples (1) are introduced into the cartridge 200 having a filter 260. Next, an electric field is applied to the transducer 220, thereby producing acoustic waves (2) of sufficient power to lyse the cells in the sample. Then, a rinsing buffer (3) is introduced into the cartridge to rinse the filter by lateral flow. Whereas the target DNA remains bound to the filter, the remaining cellular debris is transported to the waste. Optionally, the filter can be back-washed through the filter membrane. Finally, an eluant (4) is introduced into the cartridge, which displaces the target DNA from the filter and delivers the lysate having the target DNA downstream for further processing (e.g., PCR analysis, etc.).

Samples can be introduced into the cartridge in any useful manner. In one example, the sample can be a biological sample obtained from a subject (e.g., a human subject). In another example, samples can be provided as slide smears, which are processed by inserting them into a manifold 1200 (FIG. 7). The manifold is filled with a stripping buffer 1410 that removes the sample from the glass surface. The resulting solution is pumped into the cartridge using a switching syringe/distribution pump injector 1300 (PSD8, Hamilton), where intact MTB binds to the capture filter. This process concentrates the BCG on the filter support in the cartridge 1100 while eliminating a large portion of extracellular debris and harsh chemical properties of the stripping buffer. This unwanted portion can be transported to the waste 1702.

The present system can be optimized to minimize DNA loss. During final testing of the plastic cartridge, we determined through RT-PCR analysis that there were two primary sources of DNA loss: BCG retention on the filter support and non-specific DNA adsorption to the plastic surface. Data suggests that BCG is trapped where the filter is bonded to the plastic rather than retained on the filter face. Both the lateral flow and back-flow filter rinse approaches had similar recovery from the Durapore® membrane. BCG cell loss and consequently DNA loss could be mitigated by minimizing the filter bonding region. To address possible issues arising from non-specific adsorption to the plastic surface, passivation and pH adjustment can be implemented to reduce the non-specific BCG cell loss and DNA loss in the cartridge.

Loss of sample and targets could be minimized by integrating valves with the cartridge. Integrated valves can provide minimized dead volumes. Off-cartridge location of valves could result in cell and DNA loss. The Liquid-X® valve (a diaphragm-based isolation valve) was the optimal choice to process the raw BCG sample through the cartridges. For DNA extraction, the LFYA valve (a chemically inert solenoid valve) had negligible loss compared to the positive control and is ideal for the final DNA extraction step. Such valves, when integrated on-chip, could further reduce target loss.

Accordingly, the present system can provide numerous benefits. In one embodiment, each element of the acoustic array can efficiently release genomic material or proteins rather than requiring multiple elements to process them. In another embodiment, the use of a thermal exchange layer improves power handling and increases the operating frequency (e.g., from 55 to 68 MHz), which allows for continuous lysis of a sample with enhanced efficiency. In yet another embodiment, the system provides efficient recovery of the target by employing a small porous filter membrane embedded in the cartridge. Using such a filter, bacteria from large samples volumes ~10 ml could be quickly filtered and the DNA extracted within a few minutes at an efficiency of about 78%.

Example 3

Platform Having a Transducer Array

The transducer array can be adapted to be coupled reversibly to the cartridge (e.g., any described herein). In addition, the individual transducer elements in the array can be designed with any useful configuration. Described herein is a configuration in which each transducer element is disposed under one and only one channel. In this manner, each transducer can be individually controlled, and only one transducer can be activated to initiate lysing in one channel.

To achieve a much denser package, the transducers were configured as separate channels each capable of lysing. In FIG. 5A, each of the five-channel transducer elements defines one acoustic emitter capable of several power settings ranging from gentle mixing to cell membrane lysis. The acoustic transducer was fabricated from a gold (0.5 µm), 36°YX lithium niobate (50 µm), and gold (0.5 µm) film stack. Then, the stack was bonded onto a fused silica/aluminum nitride substrate lithographically patterned with 1 µm gold electrodes.

Briefly, the assembly process was as follows. First, as shown in FIG. 5A, a 1 µm gold electrode pattern 520 was defined on the AN (Valley Design Corp.) substrate 510. Then, the acoustic transducer stack was bonded to the surface of the substrate 510 using E4110 conductive epoxy (Epoxy Technology, Inc., MA). To protect the backside of the transducers, a mask was fabricated from polydimethylsiloxane (PDMS) (Dow Corning Corp., MI). A Mylar® rectangular annulus was fabricated to define the backside fill region. The backside was filled with Epo-tek® 301, a nonconductive packing sealant that covered the edges of the transducers. Finally, the transducers were back-filled with Epo-tek® E4110 conductive epoxy 530, which connects the backside of all the transducers to a common electrical node and thermally to a passive aluminum heatsink 540.

Any useful number of components can be used to provide an electrical connection to the electrodes. For instance, FIG. 5B provides an RF driver board with SMB connectors. The central region uses a plastic riser housed with spring loaded connectors (Mill-Max Mfg. Corp., Oyster Bay, N.Y.) to establish electrical connections from the PC board to the gold contacts to the electrodes.

Figure 4:
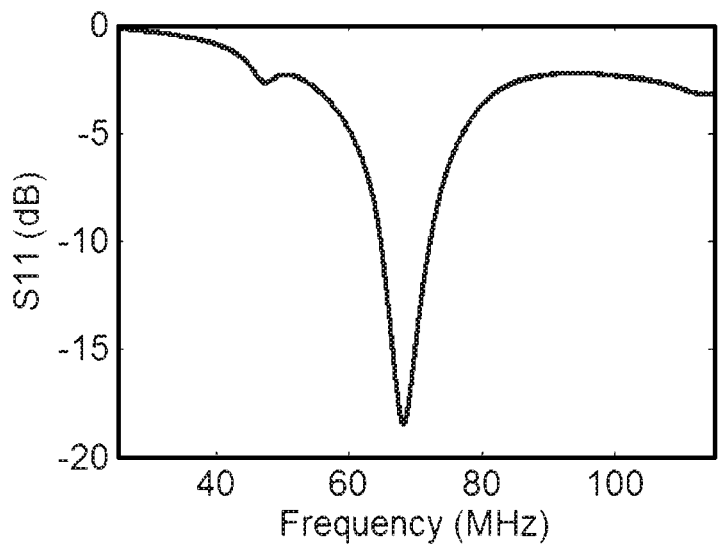
FIG. 4 is a graph showing the return loss (S11) of the single element of an exemplary lysis system operating at about 68 MHz.

The return loss of this system is provided in FIG. 4. The return loss shows excellent power transfer to the device, which has a bandwidth of 3.6 MHz. Larger bandwidths are possible with this device, albeit the return loss may degrade the power transfer, and the present invention encompasses such systems having 3.6 MHz or larger bandwidths.

Example 4

Integrated Acoustic Lysis System for Detecting Pathogenic Bacteria in Point-of-Care Diagnostics We have successfully built and verified a prototype miniature acoustic lysing system for the rapid release and extraction of DNA from bacteria. The prototype consists of two key technologies: a five channel array of miniature acoustic transducers and a disposable plastic cartridge that processes the cellular samples.

The system provides improved lysis of cells without the use of harsh lysing chemicals, while minimizing power consumption. The acoustic transducer was driven by a radio frequency (RF) signal at 68 MHz coupled to a small 2 W RF amplifier. This increase in operating frequency (i.e., from 55 MHz to 68 MHz) provided improved lysis of biological cells. In addition, the entire system can operate under battery power if needed. Typically, a small a switching power supply was used to power the unit. In one example, the electrical power required to lyse BCG samples was only 66 mW per channel.

Figure 8:
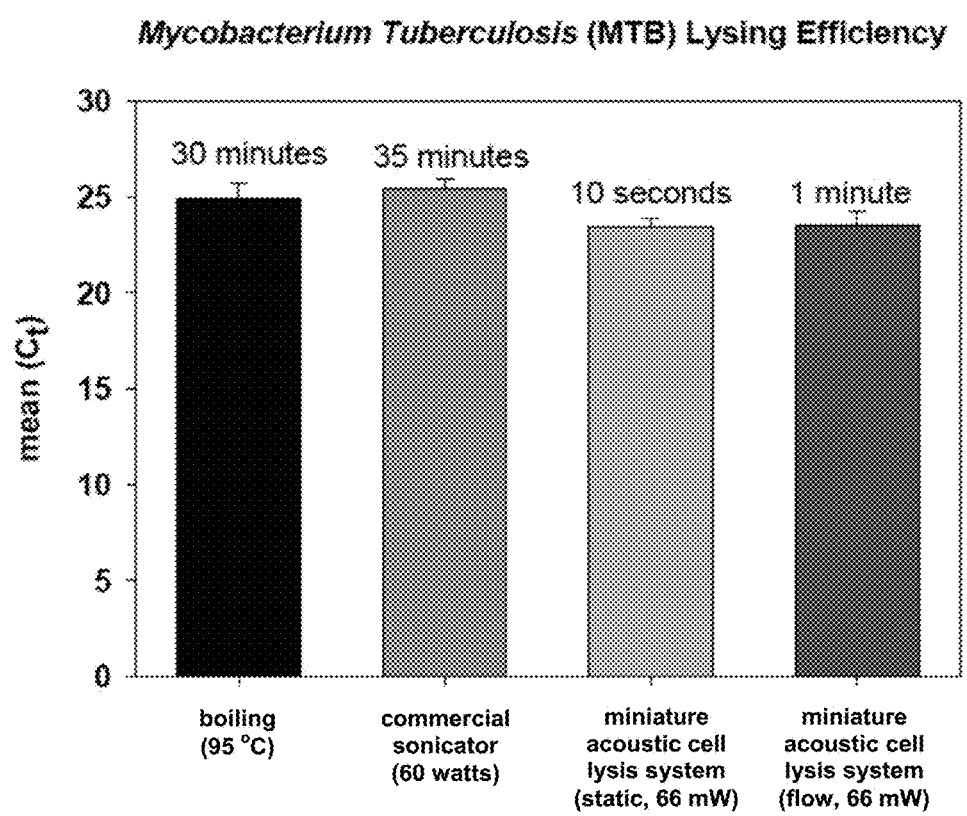
FIG. 8 is a graph showing MTB lysing efficiency using boiling, a commercial sonicator, or an exemplary system of the invention. In particular, the system herein can be employed under static conditions (i.e., fill cartridge and lyse) or flow conditions (i.e., flow during lysis). As can be seen, the system of the invention released DNA from MTB cells hundreds of times faster and at a fraction of the power compared to conventional methods. $C_t$ is the number of cycles to reach a detectable threshold concentration of target in a PCR reaction. For this relative value $C_t$, a lower value indicates that a lower number of PCR cycles are needed to detect the target. The large-scale conventional acoustic technology, a commercial sonicator, required 35 minutes to compete with the present system. Boiling was used as the control method. N=10.

In particular, the technology was used to lyse *E. coli* bacteria as well as the *M. tuberculosis* (MTB) simulant *Bacillus* Calmette-Guérin (BCG). FIG. 8 is a bar graph comparing threshold cycle ($C_t$) for the miniature acoustic cell lysis device of the present invention with boiling and a commercial tabletop sonicator ($C_t$ is a relative measure of the concentration of target in a PCR reaction—lower is better). With the miniature device, "static" refers to static filling of the lysing region during lysis and "flow" refers to fluid flowing through the lysing region during lysis.

As can be seen, the overall treatment time to release an equivalent amount of DNA from the MTB simulant BCG was 30 minutes by boiling at 95° C. (which also denatures proteins), 35 minutes for the tabletop sonicator using 60 watts, and only 1 minute for flow lysis or 10 seconds for static lysis with the miniature acoustic cell lysis device. Due to the high power density of the miniature device, only a mere 66 mW was required to lyse BCG at the same level as the positive control (i.e., boiling for 30 minutes at 95° C.). The temperature rise was only 4° C. above ambient after 30 seconds of lysing treatment at this power level.

The low power setting enables multichannel scalability, which is especially desirable for plastic disposable cartridges. In particular, disposable plastic cartridges are useful to eliminate cross contamination problems and cleaning time.

The system was also compact. Each acoustic transducer had an area of 5 mm$^2$, where the fluidic processing region scaled as 1 channel for every 5.5 cm$^2$ of cartridge space.

Overall, this technology released viable DNA, RNA, and proteins from human or bacterial cells, without chemicals or additional processing, to enable high-speed sample preparation for clinical POC medical diagnostics and use with nano/microfluidic devices. In particular, raw samples can be processed, and the lysis efficiency is comparable to commercial standards.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A miniature acoustic cell lysis system comprising:
   i) a cartridge comprising a plurality of channels, wherein each channel is configured to receive one or more test samples;
   ii) a platform comprising a transducer array, which comprises a plurality of acoustic transducers, wherein the transducer array is configured to be coupled reversibly to the cartridge and wherein each acoustic transducer is configured to be disposed beneath each channel and is adapted to propagate an acoustic wave in the channel, thereby generating localized acoustic pressure to lyse a cell by acoustic pressure; and
   iii) a thermal exchange layer configured to be disposed between the cartridge and the transducer array.

2. The system of claim 1, wherein the thermal exchange layer comprises aluminum nitride, silicon carbide, silicon nitride, boron nitride, beryllium oxide, copper, silver, gold, graphene, diamond, thermal epoxy, stainless steel, or a composite thereof.

3. The system of claim 2, wherein the thermal exchange layer is affixed to the platform and is disposed above the transducer array.

4. The system of claim 2, wherein the thermal exchange layer is affixed to the cartridge and is disposed beneath the plurality of channels.

5. The system of claim 1, wherein the cartridge is disposable and the platform is reversibly coupled to the cartridge.

6. The system of claim 1, further comprising a platen configured to maintain the cartridge in a fixed relationship with the transducer array and to enable fluidic communication with the channel.

7. The system of claim 1, wherein the operating frequency of at least one acoustic transducer is of from between 60 MHz and 80 MHz.

8. The system of claim 1, further comprising a heatsink disposed beneath the transducer array.

9. The system of claim 1, further comprising a solid support configured to be integrated within the cartridge and to be in fluidic communication with at least one of the plurality of channels.

10. The system of claim 9, wherein the cartridge comprises:
    a channel layer comprising the plurality of channels, wherein each channel comprises an inlet portion and an outlet portion;
    a top layer disposed above the channel layer, wherein the top layer comprises a plurality of inlet ports in fluidic communication with each inlet portion and a plurality of outlet ports in fluidic communication with each outlet portion; and
    a filter layer disposed between the channel layer and top layer, wherein the filter layer comprises a plurality of solid supports and each solid support is configured to be in fluidic communication with each channel.

11. The system of claim 10, wherein a coupling layer is disposed beneath the channel layer and is configured to be coupled reversibly to the thermal exchange layer.

12. The system of claim 10, wherein the solid support comprises a filter, a bead, a membrane, or a gel exclusion media.

13. The system of claim 1, wherein the cartridge comprises an inlet and an outlet both in fluidic communication with at least one channel, and wherein an integrated valve is in fluidic communication with each of the inlet and the outlet.

14. The system of claim 13, further comprising a pumping system in fluidic communication with the inlet.

15. The system of claim 1, wherein the platform comprises a transducer substrate comprising a plurality of electrodes, and wherein each electrode is electrically connected to each acoustic transducer; and a radiofrequency driver board comprising one or more contact pads configured to be electrically connected to each of the plurality of electrodes.

16. The system of claim 15, wherein the platform further comprises a radiofrequency circuit configured to provide a radiofrequency signal to the driver board.

17. The system of claim 1, further comprising an acoustic reflector disposed on a top surface of at least one channel, wherein the acoustic reflector is adapted to create a standing wave within the channel and between the acoustic reflector and at least one acoustic transducer.

18. The system of claim 17, wherein the at least one acoustic transducer is a low frequency transducer.

19. The system of claim 1, wherein the cartridge further comprises one or more reagents on-chip.

20. A miniature acoustic cell lysis system comprising:
    a cartridge comprising a plurality of channels, wherein each channel is configured to receive one or more test samples;
    a platform comprising a transducer array, which comprises a plurality of acoustic transducers, wherein the transducer array is configured to be coupled reversibly to the cartridge and wherein each acoustic transducer is configured to be disposed beneath each channel and is adapted to propagate an acoustic wave in the channel; and
    a thermal exchange layer configured to be disposed between the cartridge and the transducer array.

21. The system of claim 20, wherein the thermal exchange layer comprises aluminum nitride, silicon carbide, silicon nitride, boron nitride, beryllium oxide, copper, silver, gold, graphene, diamond, thermal epoxy, stainless steel, or a composite thereof.

22. The system of claim 21, wherein the thermal exchange layer is above the transducer array.

23. The system of claim 21, wherein the thermal exchange layer is disposed beneath the plurality of channels.

24. The system of claim 20, wherein the cartridge is disposable.

25. A miniature acoustic cell lysis system comprising:
    a cartridge comprising a plurality of channels, wherein each channel is configured to receive one or more test samples;
    a platform comprising a transducer array, which comprises a plurality of acoustic transducers, wherein the transducer array is configured to be coupled reversibly to the cartridge and wherein each acoustic transducer is configured to be disposed beneath each channel and is adapted to propagate an acoustic wave in the channel; and
    a thermal exchange layer configured to be disposed between the cartridge and the transducer array,
    wherein the operating frequency of at least one acoustic transducer ranges from 60 MHz to 80 MHz.

* * * * *